US007763257B2

(12) United States Patent
Juneau et al.

(10) Patent No.: US 7,763,257 B2
(45) Date of Patent: Jul. 27, 2010

(54) COMPOSITIONS COMPRISING TRANSFORMING GROWTH FACTOR (TGF)-β1 AND TGF-β2 IN ADMIXTURE OF PROTEINS OBTAINED FROM DAIRY PRODUCTS

(76) Inventors: Christina Juneau, 103, Des Rapides, Pont-Rouge (Québec) (CA) G3H 2A2; Réjean Drouin, 6704, rue Des Bourraches, Québec (Québec) (CA) G2C 1J1; Yves Pouliot, 7330, rue Des Mésanges, Charny (Québec) (CA) G6X 3P8; Najat Aattouri, 1611, 7e rue, Saint-Rédempteur (Québec) (CA) G6K 1S7; Sylvie Gauthier, 7330, rue Des Mésanges, Charny (Québec) (CA) G6X 3P8; Eric Lamiot, 1825, rue Desroches, Québec (Québec) (CA) G1J 1T4

( * ) Notice: Subject to any disclaimer, the term of this patent is extended or adjusted under 35 U.S.C. 154(b) by 0 days.

(21) Appl. No.: 11/695,757

(22) Filed: Apr. 3, 2007

(65) Prior Publication Data
US 2008/0031969 A1 Feb. 7, 2008

Related U.S. Application Data

(63) Continuation-in-part of application No. 11/007,912, filed on Dec. 9, 2004, now abandoned, and a continuation-in-part of application No. PCT/CA2006/001637, filed on Oct. 4, 2006.

(60) Provisional application No. 60/722,969, filed on Oct. 4, 2005.

(51) Int. Cl.
*A61K 39/00* (2006.01)
*A61K 38/00* (2006.01)
*A61K 38/27* (2006.01)
*C07K 17/00* (2006.01)
*C07K 2/00* (2006.01)

(52) U.S. Cl. .................. 424/198.1; 514/21; 514/12; 530/399; 530/351; 530/365

(58) Field of Classification Search ........................ None
See application file for complete search history.

(56) References Cited

U.S. PATENT DOCUMENTS

| 4,461,725 | A | * | 7/1984 | Mitchell ..................... 530/365 |
| 4,985,434 | A | | 1/1991 | Secrist, III et al. |
| 5,008,265 | A | | 4/1991 | Secrist, III et al. |
| 5,008,270 | A | | 4/1991 | Secrist, III et al. |
| 5,339,977 | A | | 8/1994 | Schormair et al. |
| 5,461,033 | A | | 10/1995 | Donnet et al. |
| 5,952,295 | A | | 9/1999 | Arnaud-Battandier et al. |
| 6,403,562 | B1 | | 6/2002 | Johnson et al. |
| 6,649,168 | B2 | | 11/2003 | Arvinte et al. |
| 2003/0003133 | A1 | * | 1/2003 | Schneider ................... 424/439 |
| 2004/0097714 | A1 | | 5/2004 | Maubois et al. |
| 2006/0127493 | A1 | | 6/2006 | Pouliot et al. |
| 2007/0292491 | A1 | * | 12/2007 | Hansen et al. ............... 424/448 |

FOREIGN PATENT DOCUMENTS

| CA | 1265445 | 2/1990 |
| EP | 0527283 | 11/1997 |
| FR | 282790 | * 7/2001 |
| JP | 6145069 | 5/1994 |
| WO | 9010631 | 9/1990 |
| WO | 9321187 | 10/1993 |
| WO | 9501355 | 1/1995 |
| WO | 03006500 | 1/2003 |
| WO | 03103705 | 12/2003 |
| WO | 2004004750 | 1/2004 |

OTHER PUBLICATIONS

Drouin et al, 2007. Can J. Physiol. Pharmacol. 85:943-951.*
Advitech inc., "Final Prospectus", Jun. 30, 2004.
Database WPI Week 2003, Derwent Publications Ltd., London, GB; AN 2003-561912, XP001277085, & JP 2003 089629 A (Kakunai Juyotai Kenkyusho) Sep. 18, 2001, see abstract and claims 1, 2 and 10 of the translated patent.
Doi H. et al., 2003, "Downregulation of TGF-B isoforms and their receptors contributes to keratinocyte hyperproliferatio in psoriasis vulgaris.", Journal of Dermatology Sciences, 33: 7-16.
Lebwohl M., 2003, Psoriasis, Seminar, The Lancet, vol. 361, pp. 1197-1203.
In re Brown and Saffer, 59 C.C.P.A. 1036, 459 F. 2d. 531, 1972 CCPA Lexis 325; 173 U.S.P.Q. (BNA).
"Biocryst's Topical Treatment for Psoriasis Fails in Phase III", Randal Osborne, BioWorld Today, Sep. 29, 1997.
www.canbiotec.com/CommonData/newsfiles/2nd%STUDY%20FINAL%20Results%20.pdf., downloaded Oct. 11, 2006.
Schon et al., 2005, New England Journal, 352: 1899-1912.
Belford et al., 1997, Journal of Endocrinology, 154: 45-55.
www.advitech.com/en/produits.php, downloaded Oct. 11, 2006.
www.advitech.com/en/profil.php, downloaded Oct. 11, 2006.
Poulin Y. et al., 2006, "XP-828L in the treatment of mild to moderate psoriasis: randomized, double-blind, placebo-controlled study.", Journal of Cutaneous Medicine and Surgery, vol. 10, No. 5, pp. 1-8.
Aattouri N. et al., 2004, "Immunosuppressive Effect of a Milk-derived Extract.", Immunology 2004, Medimond S.r.l. (ed.), pp. 1-4.
Aattouri N. et al., 2004, "Immunosuppressive Effect of a Milk-derived Extract.", 12th International Congress of Immunology and 4th Annual Conference of FOCIS, Reprinted from Immunology 2004, Medimond, International Proceedings, pp. 1-4.

* cited by examiner

Primary Examiner—Gary B Nickol
Assistant Examiner—Shulamith H Shafer
(74) Attorney, Agent, or Firm—Ogilvy Renault, LLP

(57) ABSTRACT

The present invention relates to a composition and methods or uses thereof in the prophylaxis and treatment of psoriasis and other auto-immune inflammatory disorders. The composition may be comprised of TGF-β1, TGF-β2, and dairy derived proteins comprising a large proportion of β-lactoglobulin.

22 Claims, 8 Drawing Sheets

Day 1    Day 28    Day 56

Day 1    Day 28    Day 56

Day 1  Day 56  Day 84

A.

B.

COMPOSITIONS COMPRISING TRANSFORMING GROWTH FACTOR (TGF)-β1 AND TGF-β2 IN ADMIXTURE OF PROTEINS OBTAINED FROM DAIRY PRODUCTS

RELATED APPLICATIONS

This application is a continuation-in-part of U.S. patent application Ser. No. 11/007,912 filed Dec. 9, 2004, and of PCT application CA2006/001637 filed Oct. 4, 2006, designating the United States, now pending, which in turn claims priority from U.S. patent application 60/722,969 filed on Oct. 4, 2005, the specifications of which are all hereby incorporated by reference.

BACKGROUND OF THE INVENTION a) Field of the Invention

The present invention relates in general to the field of the treatment of psoriasis and related skin disorders, and more particularly to a non-toxic oral and topical formulation that includes a pharmaceutically effective amount of dairy proteins for the treatment of psoriasis and related immune system disorders.

b) Description of the Prior Art

It is not known what causes psoriasis, although there is evidence of a genetic predisposition and an autoimmune etiology. Onset may be triggered by systemic infections such as streptococcus throat, skin injury, vaccinations, and certain oral medications such as steroids. Subsequently, the immune system is thought to induce inflammation and excessive skin cell reproduction, which can be exacerbated by additional factors such as stress and diet.

In normal skin, a cell moves from the basal layer through the granular layer in 4-5 weeks. In psoriatic lesions, the time is decreased 7-10 fold because of a shortened cell cycle time, an increase in the absolute number of cells capable of proliferating, and an increased rate of division. T cell mediated immune responses appear to be responsible for the inflammation and hyperproliferation of keratinocytes. Neutrophils are found in psoriatic lesions, associated with increased levels of plasminogen activators. Psoriatic fibroblasts have increased levels of enzymes involved in collagen synthesis, secondary to expansion of the papillary dermis. Psoriatic plaques comprise HLA-DR positive keratinocytes and Langerhans cells, and activated T cells expressing elevated levels of IL-2 receptors.

The typical lesion of psoriasis is a well-demarcated erythematous plaque, covered by thick, silvery scales. Psoriasis can become so extensive as to cause exfoliative erythroderma, in which the entire epidermal surface is in a state of hyperproliferation. Gluttate psoriasis is a form of the disease following streptococcal pharyngitis, with widely distributed characteristic 1-3 cm lesions. Pustular psoriasis is characterized by numerous sterile pustules of 2-5 mm in diameter, and may lead to an acute, explosive, life-threatening episode of fever, chills, leukocytosis, hypoalbuminemia, and hypocalcemia, demanding immediate, vigorous therapy. Previously stable plaque-type psoriasis can be acutely exacerbated by viral infections, particularly HIV. Psoriasis is also associated with five different forms of psoriatic arthritis, including distal interpharangeal involvement; an asymmetric, oligoarticular pattern; a symmetric polyarthritis; arthritis mutilans; and sacroiliitis and spondylitis.

The inflammation and hyperproliferation of psoriatic tissue is associated with a different histological and antigenic profile than normal skin. A panel of anti-carbohydrate monoclonal antibodies as described in the art, can be used to compare psoriatic tissue with the surrounding dermis. The glycosylation pattern in psoriatic epithelium is changed in two ways: some carbohydrates are expressed at an earlier stage of cell maturation. In addition, certain biosynthetic precursor antigens not expressed in normal skin were found in psoriatic skin.

Classical treatments of psoriasis include calcipotriene (a vitamin $D_3$ derivative), topical coal tar preparations, systemic antimitotic agents such as methotrexate, and retinoids, particularly etretinate.

Extensive psoriasis can be treated by photosensitization with oral 8-methoxypsoralen, followed by ultraviolet A. Corticosteroids are given for psoriatic arthritis and acute attacks of pustular psoriasis. More recently, cyclosporin A has been tested in clinical trials at doses of 3-7 mg/kg with promising results, but associated with the risk of renal toxicity.

Current biotechnology approaches to psoriasis treatment relate to a direct pharmaceutical-mediated attack, either on cell proliferation or on the immune component of the disease. Japanese patent application JP 6145069 describes angiogenesis inhibitors comprising ganglioside GM3 or a GM3 analog as an active agent. At 100 μg/mL, GM3 showed growth of normal human anti-endothelial cells of $4.5 \times 10^4$ on day 5, compared with $76 \times 10^4$ in controls. U.S. Pat. No. 5,339,977 describes n-deacetyl-lysoganglioside derivatives for use as phospholipase A2 inhibitors for the treatment of proliferative and autoimmune diseases, including various forms of cancer, psoriasis, and rheumatoid arthritis.

An IL-2 fusion toxin has been developed (Seragen, Inc.) that is designed to selectively destroy activated T cells in psoriatic plaques, leaving normal cells alone. The objective is to destroy activated T cells, and thereby clear the psoriasis. A Phase II study has been performed in which test doses of 5, 10, and 15 μg/kg were administered per day. Comparable improvement was observed in patients with moderate to severe psoriasis. However, in order to obtain this response, the compound was administered three days per week for four weeks.

Various formulations containing the compound BCX-34 for psoriasis, cutaneous T cell lymphoma, and HIV infection have been tested WO 95/01355; WO 93/21187; WO 90/10631; U.S. Pat. Nos. 5,008,270, 5,008,265, and 4,985, 434). BCX-34 is a small molecule drug that inhibits purine nucleoside phosphorylase, a human enzyme believed to be involved in the proliferation of T cells. An oral formulation is being tested in an ongoing Phase I/II trial. A topical formulation advanced to the Phase III stage for both lymphoma and psoriasis. The Phase III psoriasis study showed only a 14% greater improvement in mean lesion scores in the treated group compared to placebos, which for these studies was not statistically significant.

Several drugs have been designed to treat psoriasis by targeting specific cells, specific cytokines, or specific interactions between ligands and receptors. The main advantage of these biological agents over cyclosporin and methotrexate is the absence of nephrotoxicity and hepatotoxicity, but toxic effects can take years to develop. Candidates for biological therapy will be those who cannot comply with the rigors of a phototherapy regimen or have received too much PUVA and are at risk of hepatotoxicity and nephrotoxicity.

Another product available in the art consist in a chimeric human tumor necrosis factor α monoclonal antibody derived from mouse. It is made of the human constant and mouse variable regions of the IgG antibody. This agent is administered by intravenous infusion over at least 2 h and neutralizes soluble tumor necrosis factor α bound to cell membranes. Results of several case reports attest to the efficacy of this agent in the treatment of psoriasis. Drawbacks of the drug include the need for slow intravenous infusion. A small but real proportion of patients have infusion reactions, including potentially serious reactions such as hypotension, rigors, and allergic reactions. These reactions can often be prevented by slowing down the infusion or pre-treating with antihistamines or, for some conditions, systemic corticosteroids. Neutralizing antibodies can develop, making the treatment less effective. Worse, patients who develop neutralizing antibodies are more likely to develop infusion reactions. One of the greatest concerns is the potential for infection with this tumor necrosis factor α inhibitor.

Alternatively, recombinant tumor necrosis factor α receptor fusion proteins were developed, which consist of two extracellular ligand-binding domains of the human p75 tumor necrosis factor α receptor fused to the Fc portion of human IgG1. These fusion proteins are likely effective for psoriatic arthritis and seems to be safer than cyclosporin or methotrexate with no nephrotoxicity or hepatotoxicity. Non-neutralizing antibodies occur in less than 5% of patients. Antinuclear antibodies and antibodies to double-stranded DNA have been reported, but full cases of systemic lupus erythematosus are rare. Anticardiolipin antibodies also develop but have been attributed to minor concomitant infections. Because this agent is a tumor necrosis factor α inhibitor, concern has been raised about the potential for immunosuppression leading to infection.

Humanized anti-CD11a monoclonal antibody was also developed for the treatment of moderate-to-severe plaque psoriasis and moderate-to-severe rheumatoid arthritis. It is normally administered as a subcutaneous (under the skin) injection, and is designed to inhibit the binding of immune system T-cells to other cell types and targets three key processes in the cascade of events that lead to autoimmune symptoms.

Another family of products is known in the art to prevent T cell activation by blocking the LFA-3/CD-2 pathway through binding to the CD2 receptor. It is an IV/IM administered product. Since this family of products may cause reduction in CD4+ and CD8+ T lymphocyte counts, it may not be appropriate for all individuals.

A fully human fusion protein consisting of a binding site of LFA-3 fused to the Fc portion of IgG1 CD45Ro+ memory T cells, which have a major role in development of psoriasis, maximally express CD2, a natural ligand of LFA-3 has been developed. By binding CD2, it prevents T-cell activation. Moreover, the Fc portion of the molecule engages Fc receptors on macrophages and NK cells, which results in apoptosis of the CD45RO+ T cells.

Another humanized monoclonal antibody to CD11a was developed, which is a component of LFA-1 on T cells and ICAM-1 on antigen-presenting cells that is an important co-stimulatory signal resulting in T-cell activation. ICAM-1 on endothelial cells also interacts with LFA-1 on circulating T cells, a necessary step for migration of T cells into inflamed skin. It can thus interfere with development of psoriasis by blocking T-cell migration into the skin and by preventing T-cell activation. In clinical trials, some patients developed flu-like symptoms including headache, chills, fever, nausea, vomiting, or myalgias. Symptoms arose on the day of injection or the following 2 days. These acute adverse events subsided by the third dose.

Systemic treatment has been used in patients with physically, socially, or economically disabling psoriasis that has not responded to topical treatment. The choices to date have been phototherapy or systemic drug therapy. Generally, systemic treatment has employed phototherapy with Ultraviolet B irradiation, photo chemotherapy which combines the photosensitizing drug methoxsalen with Ultraviolet A phototherapy (PUVA), methotrexate, etretinate, systemic corticosteroids, and cyclosporine. Each of these systemic treatments has variable efficacy and undesired side effects, and some of them are very toxic and present frequent relapses of the disease.

The number of different and sometimes toxic treatments employed for improvement of psoriasis symptoms is testimony to the resistant nature of this disease. Not only is moderate to severe psoriasis resistant to topical treatments, but because of its chronic and recurrent nature, systemic therapy or radiation is often required. The devastating nature of this disease is emphasized by the extent of the side effects that psoriasis sufferers are willing to endure to attain a remission to a disease that they know will recur sooner or later.

Keratinocyte function is regulated via intracellular signaling pathways triggered by growth factors and adhesion molecules. Among them, the EGF family and the TGF-β family are thought to play central roles; they provide dual mode regulation of keratinocytes growth via the proliferation-stimulating effect of EGF and the proliferation-inhibiting effect of TGF-β. TGF-βs exert a wide range of biological effects on keratinocytes, such as growth inhibition, production of extracellular matrix, and synthesis of plasminogen activator and its inhibitor (PAI 1). Among them, growth inhibition is the most prominent.

TGF-β1 and TGF-β2 are synthesized and secreted in human keratinocytes. It seems that TGF-β3 is not a major TGF-β in human keratinocytes growth. Vitamin D3 is a strong inhibitor of keratinocyte growth. The involvement of TGF-β production induced by vitamin D3 increased the expression of TGF-β2 mRNA 4 to 5 fold. In contrast, TGF-β1 mRNA and TGF-β3 mRNA were not increased. Taken together, these data suggest that the intrinsic TGF-βs regulate autonomous growth of human keratinocytes, and have demonstrated that TGF-β antagonized the acanthotic and degenerative effect of TGF-α involved in psoriatic skin, but TGF-β alone did not cause granular layers to appear in the involved psoriatic epidermis, indicating that TGF-β alone cannot normalize the psoriatic condition of the epidermis.

TGF-β is now recognized as a potent growth inhibitor for human keratinocytes. TGF-β2, which was found through the normal human epidermis, was decreased in the psoriatic epidermis. Since TGF-β is a strong growth inhibitor for human keratinocytes, this result indicates the possibility that the decrease of TGF-β2 is involved in the pathogenesis of psoriasis. Therefore, the decrease in TGF-β2 in psoriasis epidermis may induce the accelerated proliferation of keratinocytes and result in epidermal hyperplasia. TGF-β is also a potent immunosuppressive agent. So the decrease of TGF-β2 may permit propagation of an immune/inflammatory reaction in the dermis and epidermis of involved psoriasis. It has been supposed that an immune-activation triggers the growth activation of epidermal keratinocytes in psoriasis. In terms of growth regulation of keratinocytes, an involvement of two groups of growth factors and cytokines, proliferation-stimulating growth factors and proliferation-inhibitory growth factors, has been reported. EGF family growth factors (TGF-α, amphiregulin and HB-EGF), KGF and IL-6 are well known as proliferation-stimulating growth factors. TGF-β family growth factors are the major proliferation-inhibitory growth factors. The increase of TGF-α, amphiregulin and IL-6 was found in psoriasis. Autocrine- or cross-induction of EGF family growth factors may play an important role in epidermal hyperplasia.

One important group of growth factors involved in psoriasis mechanisms are the dermally-derived insulin-like growth factors (IGFs), which support keratinocyte proliferation. In particular, IGF-I and IGF-II are ubiquitous peptides each with potent mitogenic effects on a broad range of cells. Molecules of the IGF type are also known as "progression factors" promoting "competent" cells through DNA synthesis. The IGFs act through a common receptor known as the Type I or IGF-I receptor, which is tyrosine kinase linked. They are synthesized in mesenchymal tissues, including the dermis, and act on adjacent cells of mesodermal, endodermal or ectodermal origin. The regulation of their synthesis involves growth hormone (GH) in the liver, but is poorly defined in most tissues.

Particular proteins, referred to as IGF binding proteins (IGFBPs), appear to be involved in autocrine/paracrine regulation of tissue IGF availability. Six IGFBPs have so far been identified. The exact effects of the IGFBPs is not clear and observed effects in vitro have been inhibitory or stimulatory depending on the experimental method employed. There is some evidence, however, that certain IGFBPs are involved in targeting IGF-I to its cell surface receptor.

Skin, comprising epidermis and underlying dermis, has GH receptors on dermal fibroblasts. Fibroblasts synthesize IGF-I as well as IGFBPs-3, -4, -5 and -6, which may be involved in targeting IGF-I to adjacent cells as well as to the overlaying epidermis. The major epidermal cell type, the keratinocyte, does not synthesize IGF-I, but possesses IGF-I receptors and is responsive to IGF-I.

U.S. Pat. No. 7,141,262 issued to Maubois et al. discloses a method for obtaining a TGF-β enriched protein fraction in activated form. However, in contrast to the present invention, this document discloses a method and a composition that contains a majority (45 to 80%) of α-lactalbumin and which intends to limit the amount of β-lactoglobulin as much as possible (less than 11%).

Considering the state of the art described above, there is still a significant need for an effective psoriasis treatment that avoids the disadvantages associated with the currently available topical or systemic treatments.

SUMMARY OF THE INVENTION

One aim of the present invention is to provide a composition and uses thereof for the prophylaxis or treatment of psoriasis or related disorders, said composition comprising between 0.01 to 5 µg of Transforming Growth Factor-β1 (TGF-β1) and between 5 to 50 µg of TGF-β2 per gram of composition, and a total protein concentration of at least 15%, preferably at least 50% (w/w), but more preferably at least 80%, with dairy derived proteins comprising at least 30% of β-lactoglobulin, preferably at least 60%. TGF-β1 and TGF-β2 can also be dairy derived, and can be found at concentration between 0.1 to 5 µg and between 8 to 20 µg respectively per gram of composition. Preferably TGF-β1 is present between 0.2 to 1.2 µg/g of composition. Preferably TGF-β2 is present between 10 to 18 µg/g of composition.

The composition also comprises Insulin-like Growth Factor (IGF). Preferably, the concentration of IGF-1 is between 0.01 to 2 µg/g of composition.

The composition may comprises additionally between about 0.1 to 15% of minerals as defined herein after.

According to our standard observation, a fair proportion of the proteins are hydro-soluble. Preferably, over 30%, more preferably between 30 and 70% of the proteins found in the composition are hydro-soluble.

Someone skilled in the art will recognize that types of psoriasis that can be prevented or treated with the method or composition of the present invention may include one of nail psoriasis, plaque psoriasis, guttate psoriasis, erythrodermic psoriasis, pustular psoriasis, hyperkeratosis, oncholysis, or psoriatic arthritis.

Another aim of the present invention is to provide a method for preventing or treating psoriasis or related disorders comprising administering to a patient a composition comprising: between 0.01 to 5 µg of TGF-β1 and between 5 to 50 µg of TGF-β2 per gram of composition, in admixture with proteins derived from dairy products in a total protein concentration of at least 80% (w/w) of the composition.

Preferably, the method for preventing or treating psoriasis comprises administering to a patient a composition comprising: between 0.1 to 5 µg of TGF-β1 and between 8 to 20 µg of TGF-β2 per gram of composition, in admixture with proteins derived from dairy products in a total protein concentration of at least 50% (w/w) of the composition.

More preferably, the method for preventing or treating psoriasis comprises administering to a patient a composition comprising: between 0.2 to 1.2 µg of TGF-β1 and between 10 to 18 µg of TGF-β2 per gram of composition, in admixture with proteins derived from dairy products in a total protein concentration of at least 80% (w/w) of the composition.

Accordingly, one aspect of the present invention contemplates a method for ameliorating the effects of a proliferative and/or inflammatory skin disorder associated with psoriasis in a mammal, the method comprising treatment of the psoriasis and related diseases with an effective amount of a composition or chemical analogues thereof capable of having properties in preventing or treating psoriasis and related diseases.

The present invention is produced using a process carried out on starting material which is commercially available and called whey proteins (WP) defined as the proteins appearing in the supernatant of milk after precipitation at pH 4.6 or after rennet precipitation. Whey proteins can present themselves in the form of a whey protein isolate, a whey protein concentrate or other whey protein derivatives.

The process is generally defined as comprising the following steps:

a) solubilization of whey proteins to a concentration of about 5% (50 g/L) in water;

b) acid precipitation of the solution at a pH of between 4.5 and 6 and a temperature of between 20° C. and 50° C.;

c) recovery of the precipitate by centrifugation at a temperature between 20° C. and 50° C.; and d) neutralization to pH 7.

e) Optionally, the recovered material is subjected to a short pasteurization (for example about 15 seconds at about 75° C.).

f) Optionally, the retentate is ultrafiltrated.

g) Furthermore, the retentate may be spray-dried to obtain a powder that will be used "as such" or in admixture with a physiologically acceptable excipient for both in vitro and in vivo use.

For the purpose of the present invention the following terms are defined below.

The term "about" as used herein refers to a margin of + or −10% of the number indicated.

The term "psoriatic tissue" refers to tissue affected by psoriasis and affected cells contained within the tissue, but not to cells that have migrated to the site such as leukocytes. Preferably, the psoriatic tissue is from a human.

The expression "effective amount" as used herein is intended to mean an amount sufficient to effect a beneficial or desired clinical result. An effective amount can be administered in one or more doses. For purposes of this invention, an effective amount of growth factors and/or dairy derived proteins, or other composition is an amount that induces a treatment or prophylactic response against at least one psoriasis responsible factor.

The terms "polypeptide", "peptide" and "protein" are used interchangeably to refer to polymers of amino acids of any length, and may be interrupted by non-amino acids.

The terms "individual" or "subject" treated according to this invention is a vertebrate, preferably a mammal, more preferably a human. Mammals include, but are not limited to, farm animals, sport animals, rodents, primates, and pets.

The term "minerals" or "ashes" as used herein is intended to mean salt constituents and minerals at concentrations normally found in dairy products. For example, there can be different concentration of calcium, phosphorus, magnesium, potassium, sodium, chloride, sulfur, and citric acid. This also means that trace elements known in the art as found in dairy products can be assimilated or inferred therein.

Other terms used in this disclosure are explained where they arise.

DESCRIPTION OF THE PREFERRED EMBODIMENT

Figure 1:
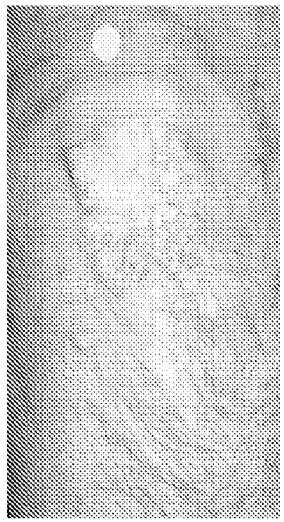
FIG. 1 illustrates elbow condition of patient no. 4 at day 1, 28 and 56 of treatment with the composition XP-828L according to one embodiment of the present invention; PASI scores were 10.2, 7.8 and 7.8 respectively.
Figure 1:
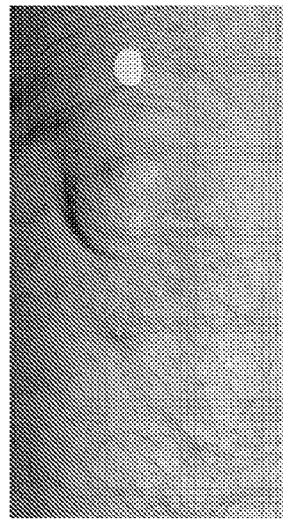
Figure 1:
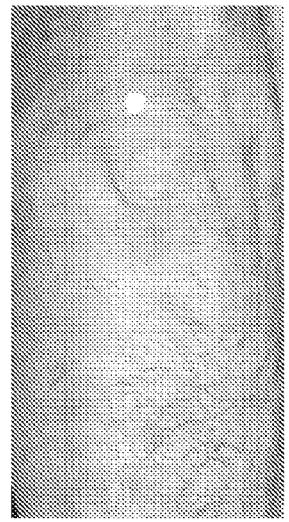
Figure 2:
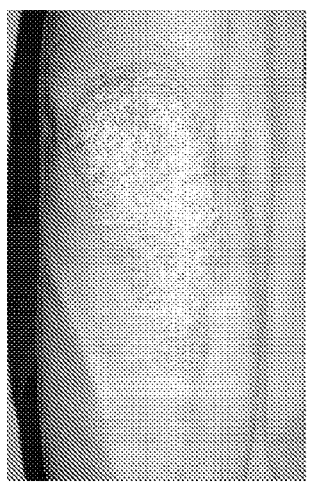
FIG. 2 illustrates elbow condition of patient no. 9 at day 1, 28 and 56 of treatment with the composition XP-828L according to one embodiment of the present invention; PASI scores were 17.4, 10.3 and 7.4 respectively.
Figure 2:
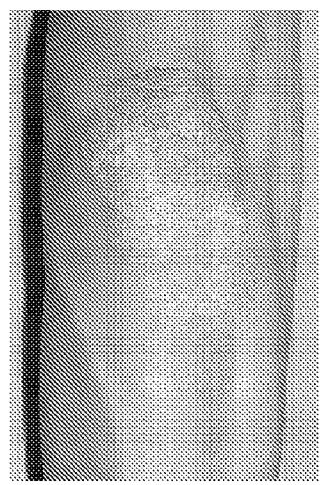
Figure 2:
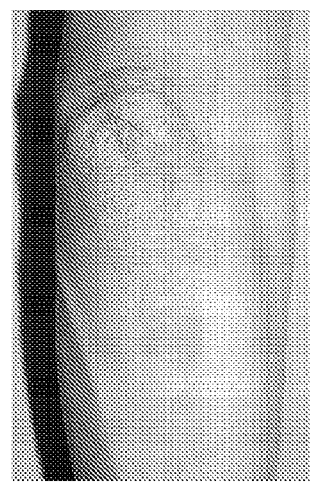
Figure 3:
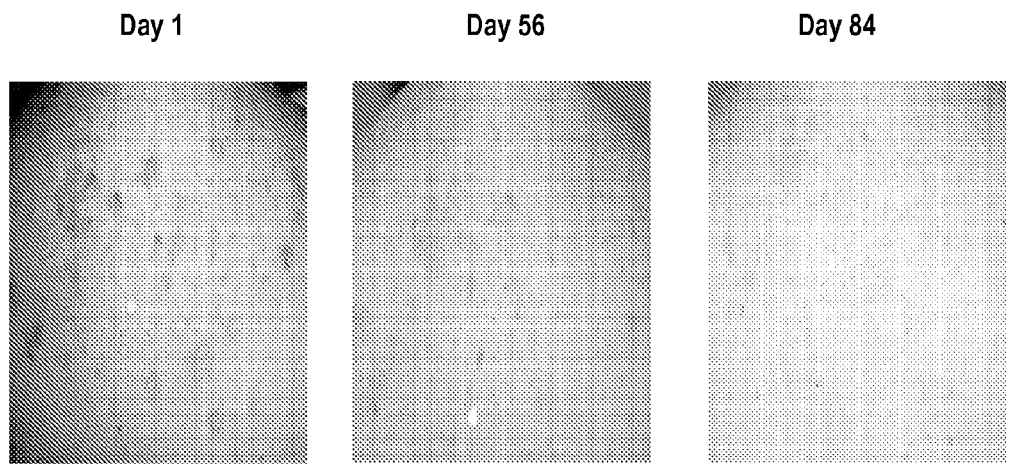
FIG. 3 illustrates back condition of patient no. 4 at day 1, 56 and 84 of treatment with the composition XP-828L according to one embodiment of the present invention; PASI scores were 10.2, 7.8 and 2.9 respectively.

The present invention now will be described more fully hereinafter with reference to the accompanying drawings, in which preferred embodiments of the invention are shown. This invention, may, however, be embodied in many different forms and should not be construed as limited to the embodiments set forth herein; rather, these embodiments are provided so that this disclosure will be thorough and complete, and will fully convey the scope of the invention to those skilled in the art.

All patents, patent applications, articles and publications mentioned herein, both supra and infra, are hereby incorporated herein by reference.

In accordance with the present invention, there is provided composition and methods for treating psoriasis in an individual, comprising administering a composition effective in stimulating a specific immunological response against a physiological imbalance aberrantly expressed in psoriatic tissue. These composition(s) comprise a cocktail of products that shares growth and regeneration characteristics of a growth factor that is aberrantly expressed in psoriatic tissue (such as human psoriatic tissue). Particular growth factors included in the composition of the present invention, but not limited thereto are transforming growth factors, such as TGF-β1 and TGF-β2, and at least 50% of dairy derived proteins. Preferably, the composition of the present invention will be comprised of more than 80% of dairy derived proteins, and most preferably more than 85% of dairy derived proteins. These dairy-derived proteins may be comprised, for example but not limited to, of between 30 to 85% (w/w) of β-lactoglobulin, preferably between 50 and 70% and most preferably at least 60%; and between 0 and 25% (w/w) of α-lactalbumin, more preferably between 5 and 15%, most preferably between 5 and 8%; and between 0 to 15% (w/w) of lactoferrin, preferably between 0 to 8%, more preferably between 4 to 5%.

Milk proteins are naturally presents as follows:

|  | grams/liter | % of total protein |
| --- | --- | --- |
| Total Protein | 33 | 100 |
| Total Caseins | 26 | 79.5 |
| alpha s1 | 10 | 30.6 |
| alpha s2 | 2.6 | 8.0 |
| beta | 9.3 | 28.4 |
| kappa | 3.3 | 10.1 |
| Total Whey Proteins | 6.3 | 19.3 |
| alpha lactalbumin | 1.2 | 3.7 |
| beta lactoglobulin | 3.2 | 9.8 |
| BSA | 0.4 | 1.2 |
| Immunoglobulins | 0.7 | 2.1 |
| Proteose peptone | 0.8 | 2.4 |

In general, the composition of the present invention typically comprises:

| Protein | Typical values | Window |
| --- | --- | --- |
| TGF-β2 | 11.5 μg/g | 8 μg/g to 20 μg/g |
| TGF-β1 | 0.3 μg/g | 0.01 to 5 μg/g |
| IGF-1 | 0.1 μg/g | 0.01 to 2 μg/g |
| β-lactoglobulin (β-Lg) | 70% | 30% to 85% |
| α-lactalbumin (α-Lac) | 6% | 0% to 25% |
| Lactoferrin (Lf) | 4.5% | 0% to 15% |
| Immunoglobulin (IgG) | 5.5% | 2% to 15% |
| Hydrosolubility | 60% | Over 30% |
| Fat | 1% | 0% et 10% |

Whey Proteins: The proteins appearing in the supernatant of milk after precipitation at pH 4.6 or after rennet precipitation are collectively called whey proteins. These globular proteins are more water soluble than caseins and are subject to heat denaturation. Native whey proteins have good gelling and whipping properties. Denaturation increases their water holding capacity. The main fractions are β-lactoglobulin, alpha-lactalbumin, bovine serum albumin (BSA), lactoferrin (Lf) and immunoglobulins (Ig).

β-Lactoglobulins: (MW-18,000; 162 residues) This group, including eight genetic variants, comprises approximately half the total whey proteins. β-Lactoglobulin has two internal disulfide bonds and one free thiol group. The conformation includes considerable secondary structure and exists naturally as a non-covalent linked dimer. At the isoelectric point (pH 3.5 to 5.2), the dimers are further associated to octamers but at pH below 3.4, they are dissociated to monomers.

alpha-Lactalbumins: (MW-14,000; 123 residues) These proteins contain eight cysteine groups, all involved in internal disulfide bonds, and four tryptophan residues. alpha-Lactalbumin has a highly ordered secondary structure, and a compact, spherical tertiary structure. Thermal denaturation and pH<4.0 result in the release of bound calcium.

Lactoferrin: Lactoferrin is a glycoprotein that belongs to the iron transporter or transferrin family. Lactoferrin belongs to the transferrin family proteins (TF, melanotransferrin, ovotransferin, etc.). Its molecular weight is 80,000 Da (80 kDa. In addition to its presence in milk, it is also found in exocrine secretions of mammals and is released from neutrophil granules during inflammation. Lactoferrin (LF) is a globular multifunctional protein with antimicrobial activity (bacteriocide, fungicide) and is part of the innate defense, mainly in mucosa. Lactoferrin is found in milk and many mucosal secretions such as tears and saliva. Human colostrum has the highest concentration, followed by human milk, then cow milk. The isoelectric point of both human breast milk lactoferrin and human granulocyte lactoferrin is 5.5-6.2.

While a detectable immunological or tissue response is likely to be beneficial, efficacy can also be deduced by an improvement in symptoms or control of the psoriatic condition beyond what would be expected without treatment.

The active composition according to the invention is distinguished by strong anti-inflammatory actions.

For prophylaxis, the active compounds are administered to a patient diagnosed with psoriasis, and prone to frequent relapse, in order to decrease manifestations of the disease in frequency and strength. Treatment in the manifest stage leads to its curtailment and to the alleviation of the symptoms.

In all types of psoriasis, the active compounds of the present composition can be used prophylactically and for the treatment of the disorders.

Estimates of the prevalence of psoriasis vary from 0.5 to 6%, with rates varying between countries and races. Different types of psoriasis can be prevented or treated with the composition of the present invention. Plaque-type psoriasis is the most common form of the disease, occurring in more than 80% of cases. Guttate psoriasis occurs in about 10% of patients with psoriasis, and erythrodermic and pustular psoriasis each occur in fewer than 3% of patients. Nail psoriasis is generally the first sign of disease in 4% of patients. Between 5 to 10% of patients with psoriasis have psoriatic arthritis, a destructive and occasionally disabling joint disease. The course of psoriatic arthritis varies, with some having mild changes and others severe, rapid destruction of joints. Skin problems such as dryness or lesions are symptoms associated with psoriasis.

Erythrodermic psoriasis is characterized by generalized inflamed erythema and widespread scaling, affecting up to 100% of the body surface area. Patients lose many of the protective functions of the skin, including the skin's ability to protect against infection, control body temperature, and prevent loss of fluids and nutrients through the cutaneous surface.

Generalized pustules psoriasis is characterized by development of sterile pustules covering large portions of the trunk and extremities. In severe cases, pustules become confluent forming large areas of pus. In this case also, many of the skin's protective functions are lost, making patients susceptible to infection and loss of fluids and nutrients.

A further neurosensory phenomenon is to be regarded as itching in the case of atopic skin, and also itching in the case of psoriasis related disorders.

According to the invention, it is therefore possible to make available active compounds and preparations containing those active compounds which, in particular, prevent neurosensory phenomena or alleviate them or rapidly make them fade, i.e. are suitable for prophylaxis and/or treatment.

"Stinging" phenomena can be regarded as disorders to be treated cosmetically or orally, or in other cases by other ways of administration. Severe itching, however, in particular in the case of atopy, in particular neurodermatitis and severe itching of the skin occurring during psoriasis, can also be regarded as a relatively serious dermatological disorder.

The active compounds according to the invention can in particular also be used on skin superficially appearing to be healthy, e.g. in the case of psoriasis and atopy, i.e. also in addition to the diseased skin areas and, in particular, here too in the case of related psoriasis disorders.

The active compounds according to the invention can also be incorporated without problems into customary oral, pharmaceutical, dermatological, and cosmetic bases for preferred oral administrations and the corresponding pharmaceutical, in particular dermatological, and cosmetic topical preparations or compositions can thus be obtained. The concentration of compounds in the composition of the present invention are adjusted depending of the needs. TGF-β1 can be found at concentration of between 0.01 to 5 μg per gram of composition and TGF-β2 can be found at concentration of between 5 to 50 μg per gram of composition. Preferably, TGF-β1 is found at concentration of 0.1 to 5 μg/g, and TGF-β2 at between 8 to 20 μg/g of composition. More preferably, TGF-β1 is found at concentration of 0.2 to 1.2 μg/g, and TGF-β2 at between 10 to 18 μg/g of composition. The preparations can be used daily in a customary manner. Preferably, the composition also comprises Insulin-like Growth Factor-1 (IGF-1) wherein the concentration of IGF-1 is between 0.01 to 2 μg/g, more preferably, between 0.05 to 1 μg/g of the composition.

In another embodiment of the present invention, the composition comprises at least 70% (w/w) of dairy derived proteins. The total concentration of proteins in the composition would preferably be of at least 80% wherein at least 60% of this protein content is β-lactoglobulin, preferably between 60% and 75%. Most preferably between 65% and 70% of total proteins is comprised of β-lactoglobulin. Dairy proteins or dairy products as used herein may include milk, colostrums, or whey proteins or derived products or fractions thereof.

The fat fraction of the composition can be generally found at concentration between about 0.05 to 10% (w/w) in the composition. Though not always the case, the fat or compounds of this family of products, can be derived from dairy products, or from any other source, such as for example, but not limited to, vegetable or animal sources, synthetic or natural sources, allowing the composition of the present invention to have its properties as defined herein. For example, the physical properties of milk fat can be summarized as follows: density at 20° C. is 915 kg/m$^3$; refractive index (589 nm) is 1.462 which decreases with increasing temperature; solubility of water in fat is 0.14% (w/w) at 20° C. and increases with increasing temperature; thermal conductivity is about 0.17 J/m/s/K at 20° C.; specific heat at 40° C. is about 2.1 kJ/kg/K; electrical conductivity is <10-12/ohm/cm; and dielectric constant is about 3.1. At room temperature, the lipids are solid, therefore, are correctly referred to as "fat" as opposed to "oil" which is liquid at room temperature. The melting points of individual triglycerides ranges from −75° C. for tributyric glycerol to 72° C. for tristearin. However, the final melting point of milk fat is at 37° C. because higher melting triglycerides dissolve in the liquid fat. This temperature is significant because 37° C. is the body temperature of the cow and the milk would need to be liquid at this temperature. The melting curves of milk fat are complicated by the diverse lipid composition: trans unsaturation increases melting points; and odd-numbered and branched chains decrease melting points.

The invention also relates to the use of the active compounds according to the invention for the production of pharmaceutical compositions, in particular oral, pharmaceutical and cosmetic compositions for the prophylaxis and treatment of psoriasis, allergies and auto-immune disorders and on dry skin and on sensitive skin.

Likewise, the invention also relates to the use of the compositions as oral, or topical preparations.

The present invention also addresses the underlying T-cell disorder that results in an inflammatory condition such as one due to psoriasis. The present inventors have recognized that most, if not all, of the current therapies for inflammatory disorders such as psoriasis or similar T-cell mediated inflammatory skin conditions are designed to modulate T-cell activity and to thereby improve symptoms of inflammation. It is possible that a major problem with the current treatments is that the therapy itself is so toxic that it may promote recurrence during healing. The toxicity of current treatments unleashes some or all of the cytokines that are associated with the promulgation of these chronic and often rebounding skin diseases.

The synergistic effects of the two TGF-β factors and dairy derived proteins result in a non-toxic, highly effective treatment for inflammatory disorders, for example psoriasis, that is without the side effects observed with virtually all other therapies for moderate to severe psoriasis (mild psoriasis may be successfully treated with proper moisturizing). As illustrated by the following studies, the most common over-the-counter treatment for psoriasis, namely coal tar, may be made more effective by the use of the present composition.

The active compounds according to the present invention can be mixed with customary pharmaceutically tolerable diluents or vehicles and, if appropriate, with other auxiliaries and administered, for example, orally or parenterally. They can preferably be administered orally in the form of granules, capsules, pills, tablets, film-coated tablets, sugar-coated tablets, syrups, emulsions, suspensions, dispersions, aerosols and solutions and also liquids, or else also as suppositories, vaginal suppositories or parenterally, e.g. in the form of solutions, emulsions or suspensions. Preparations to be administered orally can contain one or more additives such as sweeteners, aromatizing agents, colorants and preservatives. Tablets can contain the active compound mixed with customary pharmaceutically tolerable auxiliaries, for example inert diluents such as calcium carbonate, sodium carbonate, lactose and talc, granulating agents and agents which promote the disintegration of the tablets on oral administration, such as starch or alginic acid, binding agents such as starch or gelatin, lubricants such as magnesium stearate, stearic acid and talc.

Suitable excipients are, for example, lactose, sorbitol, gelatin, maize starch, stearic acid, ethanol, propylene glycol, polyethylene glycol, ethers of tetrahydrofurfuryl alcohol, microcrystalline cellulose, povidone, croscarmellose sodium, colloidal silicon dioxide, magnesium stearate, hydroxypropyl cellulose, and water.

The formulations are prepared, for example, by extending the active compounds with solvents and/or excipients, if appropriate using emulsifiers and/or dispersants, it being possible, for example, in the case of the use of water as a diluent optionally to use organic solvents as auxiliary solvents.

Administration is carried out in a customary manner, preferably orally or parenterally, in particular perlingually, sublingually, or intravenously. In the case of oral administration, apart from the excipients mentioned, tablets, of course, can also contain additives, such as sodium citrate, calcium carbonate and dicalcium phosphate together with various additives, such as starch, preferably potato starch, gelatin and the like. Furthermore, lubricants such as magnesium stearate, sodium lauryl sulphate and talc can additionally be used for tableting. In the case of aqueous suspensions and/or elixirs, which are intended for oral administration, the active compounds can be mixed, apart from with the above-mentioned auxiliaries, with various flavors enhancers or colorants.

In the case of parenteral administration, solutions of the active compounds using suitable liquid excipients can be employed.

Capsules can contain the active compound as a single constituent or mixed with a solid diluent such as calcium carbonate, calcium phosphate or kaolin. The injectable preparations are also formulated in a manner known per se.

Ointments and topical formulations are particularly of interest also when considering the use of the composition of the present invention for treating psoriasis.

The preferred compositions according to the invention can be formulated as liquid, pasty or solid preparations, for example as aqueous or alcoholic solutions, aqueous suspensions, emulsions, for example W/O or O/W emulsions, ointments, gels, lotions, creams, oils, powders or sticks. Depending on the desired formulation, the active compounds can be incorporated into pharmaceutical and cosmetic bases for topical application, which as further components contain, for example, oil components, fat and waxes, emulsifiers, anionic, cationic, ampholytic, zwitterionic and/or non-ionic surfactants, lower mono- and polyhydric alcohols, water, preservatives, buffer substances, thickeners, fragrances, colorants and opacifiers. Preferably, the emulsions, e.g. W/O emulsions, or ointments are used.

Furthermore, it is preferred according to the invention to add antioxidants to the active compounds and to the pharmaceutical and topical preparations. The use of natural or naturally identical compounds such as, for example, tocopherols is particularly preferred here. The antioxidants mentioned are contained in the compositions according to the invention, for example, in amounts from 0.01-5% by weight, in particular from 0.5-2% by weight, based on the total composition.

Process for the Production of the Composition of the Present Invention

The process is generally defined as comprising the steps as presented above. Preferably, a) whey proteins are rehydrated to a concentration of between 2% and 10% in water; b) acid precipitation of the solution is carried out at a pH of between 4.5 to 6.0 and a temperature of between 21° C. and 50° C., more preferably between 30° C. and 40° C.; c) recovery of the precipitate by centrifugation at a temperature of between 21° C. and 50° C., more preferably between 30° C. and 40° C.; d) neutralization to a pH between 6.7 to 7.3; e) the recovered material may be subjected to a short pasteurization of less than 2 minutes, preferably less than 1 minute, more preferably less than 30 seconds at a temperature of between 70° C. and 80° C., preferably between 72° C. and 78° C., more preferably between 74° C. and 76° C.; f) the retentate may be ultrafiltrated on membranes having molecular weight cut-off (MWCO) of up to a maximum of 10 kDa; and g) the retentate may be spray-dried to obtain a powder that will be used "as such" or in admixture with one or more physiologically acceptable excipient(s) for in vitro or in vivo use.

The present invention will be more readily understood by referring to the following examples which are given to illustrate the invention rather than to limit its scope.

Example I

Open-Label Clinical Efficacy of Oral Treatment

Materials and Methods

Protocol Design

This open-label study was carried out in de "Centre de Recherche Dermatologique du Québec Métropolitain". The study protocol was approved by an external ethic committee (Ethica Clinical Research inc., Montreal). All patients were submitted to a washout period of 28 days for the systemic therapies and 14 days for the topic therapies (including phototherapy) before the beginning of the study. Only tar or salicylic acid based shampoos for the scalp, mild topic corticosteroids for genital and facial areas, and an hydrating cream provided by the clinic were permitted during the washout and the treatment periods.

During the initial 56-day treatment period, 11 patients were recruited and received one pouch (5 g) of XP-828L twice a day. For the remaining of the study, the product provided by the sponsor was concentrated by a factor 2× in terms of growth factors. Therefore only 2.5 g of XP-828L were put in the pouches in order to administer the equivalent amount of growth factors on a daily basis, i.e. 60 µg of active ingredient. All patients participating at the extension study received the new lot and were informed of the introduction of the new product in the protocol.

All patients provided written informed consent. Eligible patients were at least 18 years of age and diagnosed as having active plaque psoriasis affecting at least 2% of total body surface area.

Assessments

Patients were evaluated at screening, baseline and at days 28, 56, 84 and 112 of treatment. The assessments performed at each visit are summarized in Table 1.

Psoriasis

The score for the psoriasis area-and-severity index (PASI) was the primary endpoint measured by the physician. The PASI combines assessments of psoriasis induced erythema, scaling and skin thickness, each weighed according to the size of the affected area. The composite score ranges from 0 to 72.

At each visit, the physician performed the Physician's Global Assessment (PGA), which is a general evaluation of the patient's psoriasis. The PGA uses a 5-point scale: very severe (5); severe (4); moderate (3); mild (2); almost clear (1) and absence of disease (0).

Patients also evaluated their psoriasis using the Patient's Global Assessment (Patient GA, 10-point scale) and the Pruritus Assessment (4-point scale).

The percentage of Body Surface Area (BSA) affected by psoriasis was also evaluated.

Pictures of a specific area were taken at each visit.

Evaluation of Side Effects

Side effects were evaluated in all patients. Safety measurements included the monitoring of adverse events throughout the study. In addition, vital signs (heart rate, blood pressure), eye examination, urinalysis, and blood chemistry (creatinine, albumin, total bilirubin, alanine transaminase (ALT), aspartate transaminase (AST)) were assessed. Hematology analysis (complete blood count) was also performed. Safety measurements were performed at screening, at baseline and at days 28 and 56 of treatment.

Other Anti-Psoriasis Treatments

None were authorized at the exception of tar- or salicylic acid-based shampoos or of weak corticosteroïds for application on facial lesions or genital organs.

A hydrating cream was provided to each participant for the duration of the trial. The participant were allowed to use the cream whenever needed, except during the 24 h-period before each visit.

Medication for Treatments of Conditions Other than Psoriasis

All other medication shall remain constant during the trial. If for any reason these treatments should change, the modifications were recorded in the medical dossier of the patients.

Clinical Results

A total of 11 patients, 7 males and 4 females, met the inclusion criteria and were enrolled in the study. All 11 patients completed the initial 56 days study. The age of patients ranged from 27 to 69 years old. The PASI scores at baseline ranged from 5.2 to 17.4 and the BSA with psoriasis at baseline ranged from 2 to 20%. Seven (7) out of the 11 patients were available and agreed to participate to the additional 8 weeks-extension phase.

Changes in Psoriasis Symptoms

PASI Scores

After one month of treatment, XP-828L improved the score of psoriasis area-and severity index in 6 out of 11 subjects (55%). At the end of the 56 days study, 7 of the 11 subjects (64%) had an improvement of their PASI score ranging from 9.5 to 81.3%. One patient achieved PASI 75 (at least 75% improvement in PASI relative to baseline) at day 56 of treatment.

At day 84 (extension study), 5 patients out of 7 had an improvement of the PASI score relative to baseline ranging from 6.7 to 71.6%. 3 patients of 7 had improved PASI scores at day 84 compared to day 56 of treatment. At the end of the extension study, at 112 days of treatment, PASI score improvement ranged from 6.7 to 78.4%. Another patient reached PASI 75 after 112 days of treatment. 2 patients out of 7 had a further significant reduction of their PASI score at day 112 compared to day 84 of treatment.

Body Surface Area

The body surface area affected by psoriasis did not change significantly during the trial (Table 3).

TABLE 1

Summary of the assessments at each patient's visit.

| | Day of the visit | | | | | | |
|---|---|---|---|---|---|---|---|
| | (screening) −30 | (baseline) 1 | 7 | 28 | 56 | 84 | 112 |
| Written informed consent | x | | | | | | |
| Review of criteria | x | x | x | x | x | x | x |
| Examination of skin | x | | | | | | |
| Blood pressure | x | x | x | x | x | x | x |
| Pregnancy test | x | x | x | x | x | x | x |
| Blood sample (hematology & biochemistry) | x | x | x | x | x | x | x |
| Examination of the eye | x | | | | | | x |
| Psoriasis evaluation | | | | | | | |
| % BSA | | x | | x | x | x | x |
| PASI | | x | | x | x | x | x |
| PGA | | x | | x | x | x | x |
| Patient GA | | x | | x | x | x | x |
| Pruritus | | x | | x | x | x | x |
| Photographs | | x | | x | x | x | x |
| Report of adverse effects | | | x | x | x | x | x |

One patient experienced an increase in its PASI score of 13.6%. For the other 3 patients, the PASI score remained unchanged. (Table 2).

TABLE 3

Changes in body surface area (BSA, %) during the trial.

| | BSA (%) | | | | |
|---|---|---|---|---|---|
| | Day 1 | Day 28 | Day 56 | Day 84 | Day 112 |
| Patient 1 | 6 | 6 | 6 | 6 | 6 |
| Patient 2 | 6 | 6 | 6 | 6* | — |
| Patient 3 | 11.5 | 11.5 | 11.5 | 13.5 | 13.5 |
| Patient 4 | 8 | 8 | 8 | 5 | 5 |
| Patient 6 | 6 | 6 | 6 | 6 | 6 |
| Patient 7 | 6.5 | 7 | 7.5 | — | — |
| Patient 8 | 2 | 1.75 | 1.75 | 1.75 | 1.75 |
| Patient 9 | 11.5 | 11.5 | 11.5 | 11.5 | 11.5 |
| Patient 10 | 6 | 6 | 5.8 | — | — |
| Patient 12 | 3.75 | 3.75 | 1.5 | — | — |
| Patient 13 | 20 | 20 | 20 | 20 | 20 |
| Mean ± std | 7.9 ± 4.9 | 7.95 ± 4.9 | 7.8 ± 5.2 | 8.7 ± 5.9 | 9.1 ± 6.2 |

*Patient 2 was excluded from extension study (at day 72) because of a dental surgery Psoriasis Global Assessment The PGA decreased for 2 patients (patient 4 and patient 9) after 28 days of treatment, and for 2 patients (patient 8 and patient 12) after 56 days of treatment by one point. Two patients considered that their psoriasis improved significantly with XP-828L, showed by the important decrease of the Patient GA (from 10 to 5 for patient 4 and from 6 to 4 for patient 13 at 28 days of treatment). (Table 4 and Table 5).

TABLE 2

PASI scores and changes in PASI score (%) of subjects with psoriasis treated for 56 days (11 patients) or 112 days (7 patients) with 5 g twice daily of XP-828L.

| | PASI score | | | | | Changes in PASI score (%) | | |
|---|---|---|---|---|---|---|---|---|
| | | | | | | Day 56 relative to | Day 84 relative to | Day 112 relative to |
| Patient[b] | Day 1 | Day 28 | Day 56 | Day 84 | Day 112 | baseline % | baseline % | baseline % |
| 1 | 9 | 9 | 9 | 8.4 | 8.4 | 0 | −6.7 | −6.7 |
| 2[a] | 7.2 | 6.4 | 4.8 | — | — | −33.3 | — | — |
| 3 | 14.2 | 14.2 | 14.2 | 14.2 | 14.1 | 0 | 0 | −0.7 |
| 4 | 10.2 | 7.8 | 7.8 | 2.9 | 2.2 | −23.5 | −71.6 | −78.4 |
| 6 | 8.4 | 7.6 | 7.6 | 7.6 | 5.6 | −9.5 | −9.5 | −33.3 |
| 7[c] | 7.6 | 8.5 | 8.8 | — | — | +15.8 | — | — |
| 8 | 5.2 | 4.9 | 3.7 | 3.9 | 3.7 | −28.8 | −25.0 | −28.8 |
| 9 | 17.4 | 10.3 | 7.4 | 6.6 | 6.6 | −57.5 | −62.1 | −62.1 |
| 10[c] | 10.8 | 10.4 | 8.9 | — | — | −17.6 | — | — |
| 12[c] | 5.9 | 4.3 | 1.1 | — | — | −81.3 | — | — |
| 13[d] | 11.4 | 11.4 | 11.4 | 11.4 | 11.4 | 0 | 0 | 0 |
| Mean | | | | | | −21.4 ± 28.3 | −25.0 ± 29.9 | −30 ± 30.8 |
| n | | | | | | 11 | 7 | 7 |

[a]Patient 2 was excluded from extension study (at day 72) because of a dental surgery
[b]Patients 5 and 11 were excluded at the beginning of the study
[c]Patients have refused to participate to the extension study In the extension study, the PGA and the Patient GA further decreased for patient 4 at day 112. The patient 4 continued to consider that his psoriasis was very improved (Patient GA from 10 at baseline to 3 at day 112).

TABLE 4

Changes in physician's global assessment of psoriasis (PGA) during the trial.

| | PGA | | | | |
|---|---|---|---|---|---|
| | Day 1 | Day 28 | Day 56 | Day 84 | Day 112 |
| Patient 1 | 3 | 3 | 3 | 3 | 3 |
| Patient 2 | 3 | 3 | 3 | 3* | — |
| Patient 3 | 3 | 3 | 3 | 3 | 3 |
| Patient 4 | 3 | 2 | 2 | 2 | 1 |
| Patient 6 | 3 | 3 | 3 | 3 | 3 |
| Patient 7 | 3 | 3 | 3 | — | — |
| Patient 8 | 3 | 3 | 2 | 3 | 3 |
| Patient 9 | 4 | 3 | 3 | — | — |
| Patient 10 | 3 | 3 | 3 | — | — |
| Patient 12 | 2 | 2 | 1 | — | — |
| Patient 13 | 3 | 3 | 3 | 3 | 3 |

*Patient 2 was excluded from extension study (at day 72) because of a dental surgery

TABLE 5

Changes in patient's global assessment of psoriasis (Patient GA) during the trial.

| | Patient GA | | | | |
|---|---|---|---|---|---|
| | Day 1 | Day 28 | Day 56 | Day 84 | Day 112 |
| Patient 1 | 7 | 5 | 6 | 7 | 5 |
| Patient 2 | 7 | 6 | 7 | 6* | — |
| Patient 3 | 6 | 6 | 6 | 8 | 8 |
| Patient 4 | 10 | 5 | 5 | 5 | 3 |
| Patient 6 | 6 | 6 | 6 | 6 | 6 |
| Patient 7 | 9 | 10 | 10 | — | — |
| Patient 8 | 3 | 3 | 3 | 3 | 3 |
| Patient 9 | 5 | 8 | 5 | 7 | 7 |
| Patient 10 | 8 | 8 | 10 | — | — |
| Patient 12 | 2 | 3 | 2 | — | — |
| Patient 13 | 6 | 4 | 4 | 5 | 5 |

*Patient 2 was excluded from extension study (at day 72) because of a dental surgery The pruritus scale did not change significantly during the trial. Three patients experienced a reduction of their pruritus (Table 6).

TABLE 6

Changes in pruritus reported by the patients during the trial.

| | Pruritus | | | | |
|---|---|---|---|---|---|
| | Day 1 | Day 28 | Day 56 | Day 84 | Day 112 |
| Patient 1 | 1 | 1 | 1 | 1 | 1 |
| Patient 2 | 1 | 1 | 1 | 1* | — |
| Patient 3 | 1 | 1 | 1 | 1 | 1 |
| Patient 4 | 2 | 2 | 1 | 1 | 1 |
| Patient 6 | 2 | 1 | 1 | 1 | 1 |
| Patient 7 | 1 | 2 | 3 | — | — |
| Patient 8 | 3 | 2 | 3 | 3 | 3 |
| Patient 9 | 1 | 1 | 0 | 1 | 1 |
| Patient 10 | 2 | 3 | 2 | — | — |
| Patient 12 | 1 | 1 | 1 | — | — |
| Patient 13 | 1 | 1 | 1 | 0 | 0 |

*Patient 2 was excluded from extension study (at day 72) because of a dental surgery Changes in Hematology & Biochemical Measurements XP-828L was well tolerated. No clinically significant laboratory abnormalities or pattern of changes in vital signs were observed during the XP-828L treatment.

Table 7 reports the data for creatinine, ALT and AST. It can be noticed that two ALT values for patient 3 were out of range at days 28 (ALT=63) and 56 (ALT=62). These fluctuations were not considered significant since all other values for patient 3 were within ranges.

Also, two patients (patients 12 and 13) experienced not clinically significant temporary fluctuations in creatinine values during the trial. In each case, a new blood test 2-4 days later showed creatinine values back to normal.

No clinically significant adverse events were reported during the treatment.

TABLE 7

Safety of XP-828L as expressed by creatinine, ALT, AST and Hb data collected during the trial.

| | Creatinine (normal value: 50-100) | | | | | ALT (normal value: 0-42) | | | | |
|---|---|---|---|---|---|---|---|---|---|---|
| Patient | Day 1 | Day 28 | Day 56 | Day 84 | Day 112 | Day 1 | Day 28 | Day 56 | Day 84 | Day 112 |
| 1 | 71 | 86 | 82 | 75 | 80 | 15 | 14 | 14 | 16 | 12 |
| 2[a] | 88 | 91 | 87 | 85* | — | 12 | 14 | 10 | 13* | — |
| 3 | 91 | 87 | 90 | 87 | 89 | 26 | 63 | 62 | 26 | 36 |
| 4 | 98 | 103 | 103 | 102 | 106 | 31 | 28 | 30 | 28 | 28 |
| 6 | 70 | 75 | 67 | 72 | 70 | 12 | 13 | 10 | 11 | 9 |
| 7[b] | 77 | 73 | 77 | — | — | 8 | 9 | 10 | — | — |
| 8 | 97 | 94 | 87 | 82 | 96 | 32 | 30 | 28 | 42 | 37 |
| 9 | 107 | 100 | 105 | 104 | 96 | 21 | 20 | 21 | 18 | 23 |
| 10[c] | 95 | 104 | 95 | — | — | 17 | 19 | 16 | — | — |
| 12[c] | 102 | 104 | 113 | — | — | 17 | 19 | 18 | — | — |
| 13 | 89 | 85 | 92 | 85 | 89 | 24 | 27 | 41 | 32 | 53 |
| Mean | 90 | 91 | 82 | 87 | 90 | 20 | 19 | 19.7 | 20 | 24 |
| SD | 12 | 11 | 27 | 11 | 13 | 8 | 7 | 9.3 | 10 | 12 |

TABLE 7-continued

Safety of XP-828L as expressed by creatinine, ALT, AST and Hb data collected during the trial.

| Patient | AST (normal value: 0-40) | | | | | Hb (normal value: 120-160) | | | | |
|---|---|---|---|---|---|---|---|---|---|---|
| | Day 1 | Day 28 | Day 56 | Day 84 | Day 112 | Day 1 | Day 28 | Day 56 | Day 84 | Day 112 |
| 1 | 27 | 18 | 18 | 21 | 19 | 126 | 124 | 121 | 121 | 116 |
| 2[a] | 24 | 23 | 21 | 25* | — | 132 | 133 | 130 | 129* | — |
| 3 | 28 | 33 | 41 | 24 | 26 | 146 | 143 | 157 | 154 | 154 |
| 4 | 26 | 23 | 30 | 30 | 28 | 151 | 145 | 146 | 146 | 148 |
| 6 | 19 | 15 | 16 | 21 | 14 | 134 | 130 | 130 | 133 | 131 |
| 7[b] | 16 | 15 | 18 | — | — | 140 | 141 | 143 | — | — |
| 8 | 23 | 21 | 23 | 36 | 25 | 161 | 154 | 158 | 159 | 151 |
| 9 | 23 | 22 | 27 | 22 | 18 | 146 | 149 | 146 | 145 | 144 |
| 10[c] | 16 | 17 | 19 | — | — | 152 | 150 | 151 | — | — |
| 12[c] | 24 | 20 | 21 | — | — | 156 | 157 | 154 | — | — |
| 13 | 26 | 30 | 36 | 36 | 45 | 152 | 156 | 153 | 148 | 151 |
| Mean | 23 | 22 | 25 | 27 | 22 | 145 | 144 | 145 | 142 | 141 |
| SD | 4 | 6 | 8 | 6 | 6 | 11 | 11 | 12 | 13 | 15 |

*Patient 2 was excluded from extension study (at day 72) because of a dental surgery Efficacy of XP-828L In this open label study on patients with mild-to-moderate chronic plaque psoriasis, XP-828L treatment for 56 days showed to improve psoriasis. Scores for the psoriasis area- and severity index started to decrease after one month of treatment which can be considered a remarkable achievement for a natural health product. Two patients have reached PASI 75, one after 56 days of treatment and one after 112 days of treatment.

The extent of PASI scores reduction was generally lower during the extension period. As shown in Table 2, the average decrease in PASI scores was 21.5% at day 56 and 25% at day 112. The other parameters (PGA, patient's global assessment, pruritus) remained stable during the extension study. This might suggest that the efficacy of XP-828L has reached its maximum after day 56 in the dosage of the study. It also shows that the improvements of XP-828L on psoriasis are preserved during the extension period.

No patient experienced a complete elimination of the psoriasis symptoms, suggesting perhaps that we are in an effective range of treatment but certainly in a sub-optimal dosage (higher or lower dosages may be more effective, see examples VI, VII and VIII).

Safety of XP-828L

Since there were no clinical significant side effects or adverse events with the use of XP-828L for 112 days, it is suggested that XP-828L may represent a safe way to treat psoriasis. Only one patient experienced fluctuations of his creatinine values but no fluctuation pattern was found and no other abnormalities were observed.

The main findings of this open label study are:

XP-828L showed to have the potential of improving psoriasis on patients with mild-to-moderate chronic plaque psoriasis. PASI scores already started to decrease after 28 days of treatment in some patients.

No clinically significant adverse events or laboratory abnormalities were observed during the XP-828L treatment. These results suggest that XP-828L is safe.

Overall, the tolerability of XP-828L was good. Patients reported that they liked the product and found its use very convenient.

Example II

Preparation of Composition 1000 kg of a whey protein isolate was rehydrated up to 5% (50 g/L) in deionized water and stabilized overnight at 4° C. under agitation. The pH of the solution was adjusted to between 4.8 and 5.2 by addition of concentrated HCl. This adjustment induced protein precipitation. The precipitate was then recovered by centrifugation on a Westfalia separator at 11 $m^3$ per hour and washed with acidified water. The precipitate was rehydrated to obtain 800 liters, which was thermally treated at 75° C. during 15 seconds, before concentration and spray drying. Approximately 60 kg of composition was obtained.

Example III

Analysis of the Composition

Typical content of the composition is presented in table 8. Proteins were analyzed by the Kjeldahl Method and Dye Binding Method (AOAC Official Method 930.29; AOAC Official Methods of Analysis (1995)), while fat content was quantified by the Roese-Gottlieb Method (AOAC Official Method 932.06), humidity by drying in a dry oven, beta-lactoglobulin and α-lactalbumin by RP-HPLC and growth factors by ELISA methods.

TABLE 8

Typical analysis of the composition

| Compound | Quantity (w/w) |
|---|---|
| Proteins (hydro-soluble proteins) | 90% (48%) |
| α-lactalbumin | 6% |
| β-lactoglobulin | 66% of total proteins |
| IGF-1 | 0.1 μg/g of the composition |
| TGF-β2 | 11.7 μg/g of the composition |

TABLE 8-continued

Typical analysis of the composition

| Compound | Quantity (w/w) |
|---|---|
| TGF-β1 | 0.3 µg/g of the composition |
| Fat | 1.9% |
| Humidity | 4.2% |
| Ashes | 2% |

Example IV

Typical Analysis of XP-828L

TGF-β2: Concentration of 11.5 µg/g of powder.
Typical inhibition of murine splenocyte proliferation:
1 µg/ml=inhibition from −5 to 10%
10 µg/ml=inhibition from 5 to 20%
100 µg/ml=inhibition from 20 to 45%
1000 µg/ml=inhibition from 45 to 75%

Example V

Inhibition of Proliferation of Mice Splenocytes

TGF-β has multiple immunosuppressive effects at the cellular level and has been described as inhibiting type 1 and type 2 cells, B cells, T cells, macrophages and natural killer cells. TGF-β blocks cell-cycle progression and may have a direct effect on expression of the gene encoding IL-2. Importantly, it can suppress the expression of IL-12 and IL-2 receptors, as well as down-regulate MHC (major histocompatibility complex) class II expression on macrophages (specifically by antagonizing TNF-α and IFN-γ). The importance of TGF-β in the induction and maintenance of normal tolerance has been illustrated by TGF-β-knockout mice, who incur severe, spontaneous, multi-organ, autoimmune disease associated with autoantibody production, which proves fatal in early life. T lymphocytes isolated from murine spleen (splenocytes) are immune cells that respond to ConA (mitogenic stress) by proliferation and cytokines production. The purpose of this example was to evaluate the inhibition effect of the composition produced in example II and described in example III on splenocytes proliferation and production of pro-inflammatory cytokines, and try to elucidate some aspects of the composition's mechanism of action.

Female BALB/c mice, 6-8 weeks old, were obtained from Charles River (Montreal, Canada). Mice were sacrificed by $CO_2$ inhalation and single-cell suspensions were prepared individually from murine spleen under aseptic conditions. Murine lymphocytes ($1.25 \times 10^6$ cells/ml) were treated with ConA (1.25 µg/ml) for 72 hours. Alamar Blue® was added 24 hours before measuring ConA-induced lymphocytes proliferation. Cytokines (IL-2 & IFN-γ) levels were also determined in the supernatant following the incubation period. BSA was used as a protein control (1-1000 µg/ml).

Figure 4:
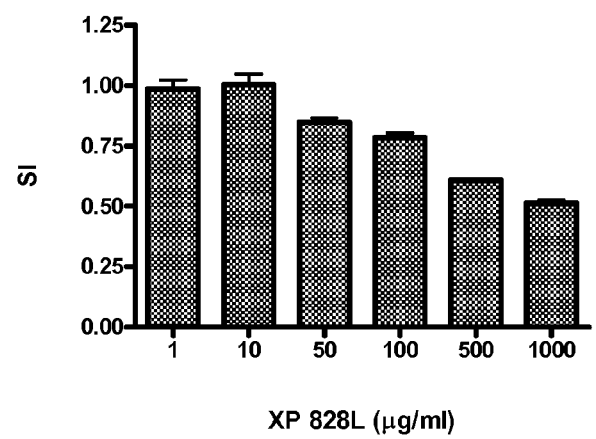
FIG. 4 shows a dose-dependent inhibition of ConA-induced murine splenocytes proliferation by the composition of the present invention as described in detail in example V.
Figure 5:
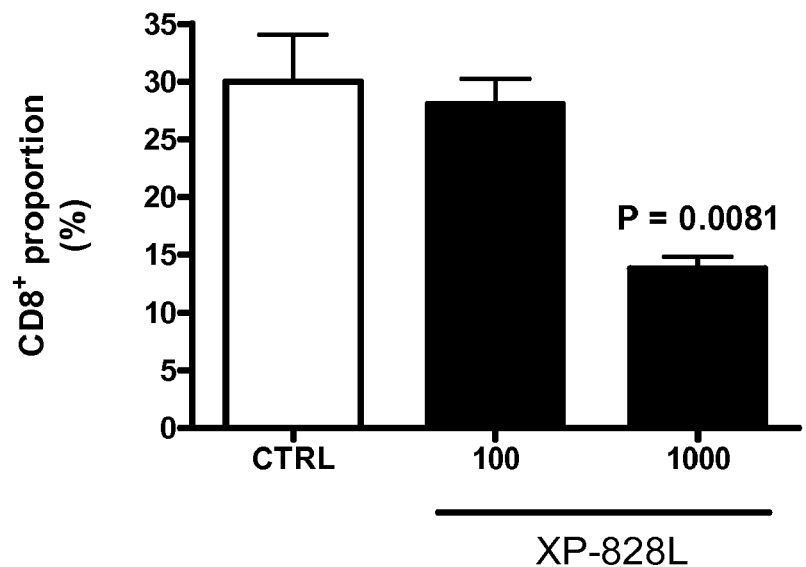
FIG. 5 illustrates the effect of the composition of the present invention on CD8+ proportion in ConA-activated mice splenocytes. Cells were incubated for 72 h in the presence of 1.25 μg/ml of ConA. Data are expressed as means±SD as described in detail in example V.
Figure 6:
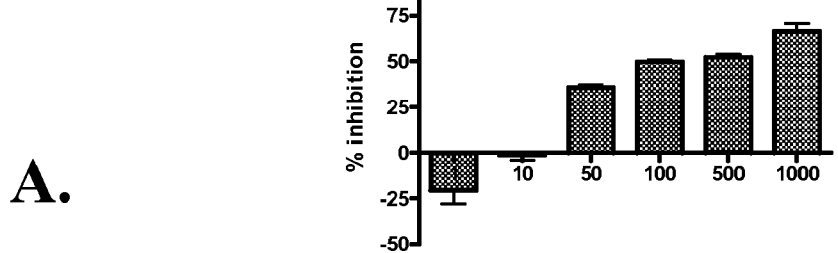
FIG. 6 shows a dose-dependent inhibition of ConA-induced murine splenocytes IL-2 production (A) and IFN-γ production (B) by the composition produced in example II and described in example III with the experimental details as described in example V.
Figure 6:
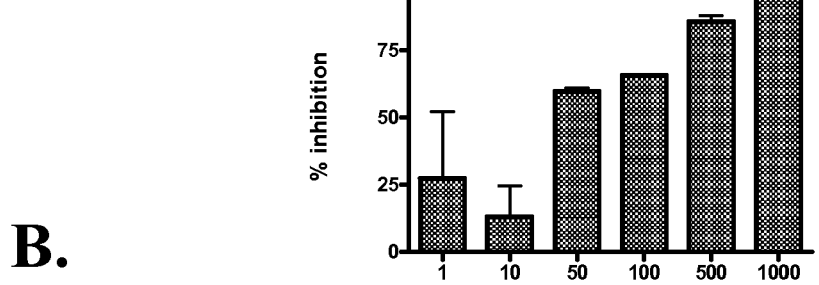

The composition produced in example II and described in example III (1, 10, 50, 100, 500, and 1000 µg of the total composition per ml of culture medium), was added to the cells for the whole incubation period and dose-dependently decreased 1) the lymphocyte proliferation (FIG. 4) the proportion of CD8 lymphocytes (FIG. 5), and the production of IL-2 and IFN-γ (FIG. 6). As shown in FIG. 4, there was a significant inhibition of induced proliferation by the composition. Without wishing to be bound to theory, these results suggest that the composition presents immunomodulatory functions and that it can be use to address immune-mediated chronic inflammatory diseases such as psoriasis, inflammatory bowel diseases and related arthropathies.

Example VI

Test on TNBS-Induced Inflammation in Healthy Rats

Inflammatory bowel diseases (IBD) is a term used to describe a collection of diseases that involve the intestine and are characterized by chronic inflammation, sometimes accompanied by ulceration in the small or large intestine. Cytokines play an important role in modulating the immune system since they are rapidly synthesized and secreted from activated inflammatory cells and induce the production of adhesion molecules and other inflammatory mediators, such as reactive oxygen metabolites, nitric oxide, and lipid mediators. Cytokines induce, amplify, prolong, and inhibit inflammation. Recently, several murine models of colitis have been developed which have highlighted the important role that abnormalities of the immune system, particularly those affecting T cells, may play in disease pathogenesis. The purpose of this example was to characterize the effect of local application of the composition produced in example II and described in example III on TNBS-induced colitis in rats.

Male Sprague Dawley (Charles River Laboratories, Montreal), were kept in individual cages, at 20° C. and 55% relative humidity with 12 h light/dark cycles, in a facility meeting the Canadian Council on Animal Care guidelines. The rats were subjected to a 24-hour starving period prior to inflammatory stress induction. Colonic inflammation was induced by using a technique from Togawa et al. Briefly, the rats were lightly anesthetized with isoflurane after overnight food deprivation, and a polyethylene catheter was inserted 8 cm into the colon via the anus. TNBS (Sigma-Aldrich, Canada) dissolved in 50% (vol/vol) aqueous ethanol (25 mg/ml) was injected into the colon (total volume of 1 ml/rat). The control rats received 1 ml of PBS intracolonically in place of TNBS and ethanol.

Three groups of rats were treated in the following manner:

Group 1: Non-stressed control receiving 2 ml of PBS (n=2) once a day throughout the protocol;

Group 2: Stressed control: TNBS (stress agent) in the intestinal lumen receiving 2 ml of PBS once a day, 5 days prior to administration of the stress agent in the lumen and 24 hours following the administration of the stress agent in the lumen (n=8);

Group 3: Colorectal administration of the composition produced in example II and described in example III (78.2 mg/kg in 2 ml of PBS, n=7) once a day, 5 days prior to administration of the stress agent in the lumen and 24 hours following the administration of the stress agent in the lumen.

Figure 7:
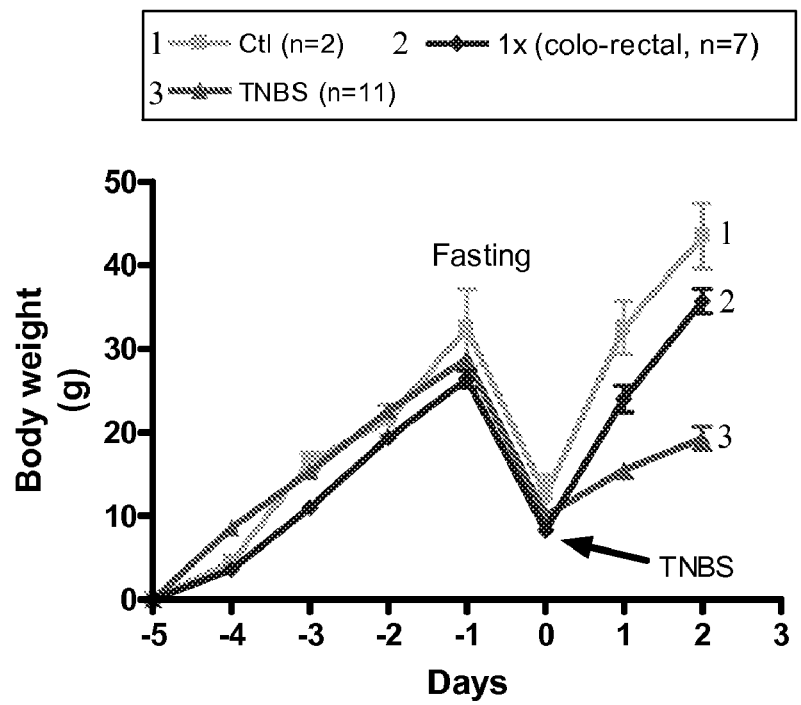
FIG. 7 illustrates the effect of colorectal administrations of the composition produced in example II (at a dose of 78.2 mg/kg=1×) and described in example III on daily body weight variations of Sprague-Dawley rats treated with 2,4,6-trinitrobenzenesulfonic acid (TNBS), a chemical inflammatory inducer, as described in detail in example VI.

Animals were weighed every day for the entire time of the protocol. Forty-eight hours following the TNBS administration, the rats were sacrificed and a 1 cm excision of the intestine was sampled. Samples were weighed and macroscopic colonic damage was scored by the following scale:
0. No damage
1. Localized hyperemia, no ulcer
2. Ulcerations without hyperemia of bowel wall thickening
3. Ulceration with inflammation at one site
4. Two or more sites of ulceration/inflammation
5. Major sites of damage extending more than 1 cm along the length of colon
6-10. If damage extends more than 2 cm along length of colon, score is increased by one for each additional 1 cm Body weight. As shown in FIG. 7, body weights of the animal increased constantly prior to fasting and TNBS injection in all groups. Following PBS injection (for control animals only), animals regained the weight lost during the fasting period. In TNBS-treated animals, however, the animals did not regain the body weight lost during the fasting period. As for the animals treated with the composition produced in example II and described in example III, body weight was increased following the TNBS injection.

Figure 8:
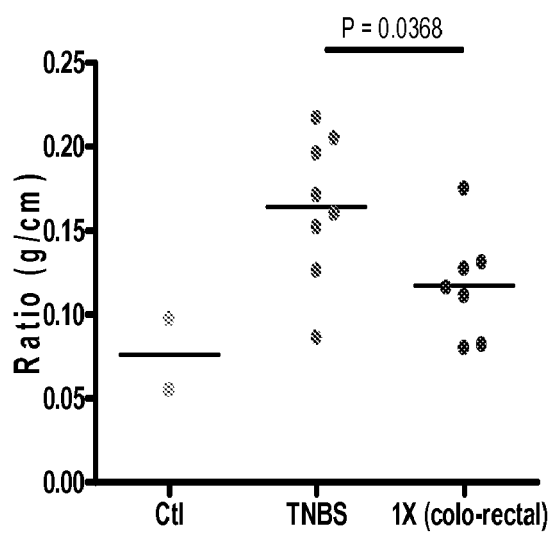
FIG. 8 illustrates the effects of colorectal administrations of the composition produced in example II and described in example III on weight-to-length ratios of the colons of Sprague-Dawley rats treated with TNBS, as described in detail in example VI.

Weight-to-length ratio. TNBS injection increased weight-to-length ratio in colon for both TNBS and the composition produced in example II and described in example III groups, indicating the presence of inflammation and edema. However, the increase was significantly ($P<0.05$) inferior in animals treated with the composition produced in example II and described in example III than in TNBS-treated animals (FIG. 8).

Figure 9:
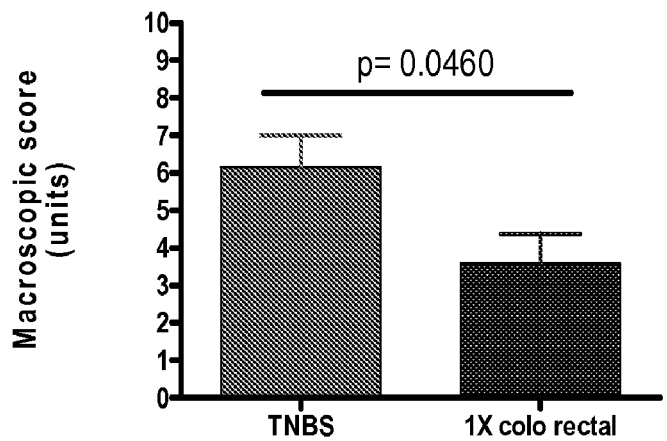
FIG. 9 illustrates the effects of colorectal administrations of the composition produced in example II and described in example III on macroscopic damages of rat colon tissues previously irritated with TNBS, as described in detail in example VI.
Figure 10:
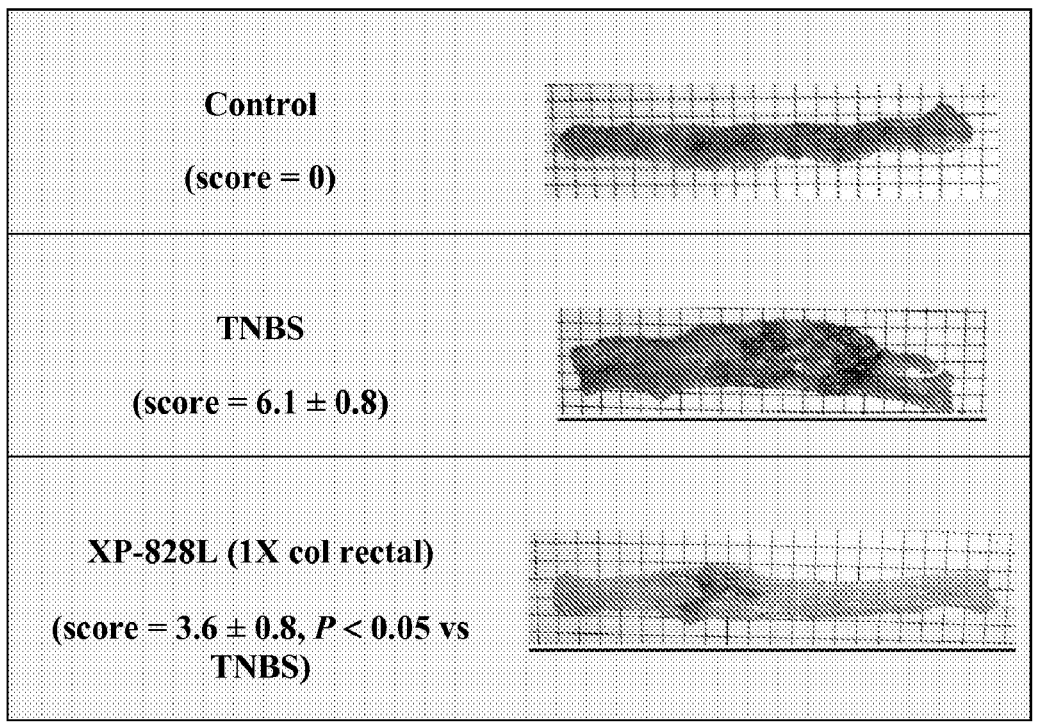
FIG. 10 illustrates the effects of the composition produced in example II and described in example III on the macroscopic appearance of lesions in TNBS colitis, as described in detail in example VI.

Macroscopic scores. TNBS injection increased macroscopic scores of inflammation in both groups treated with either TNBS and the composition produced in example II and described in example III, indicating the presence of inflammation and edema. However, the increase was significantly inferior ($P<0.05$) in animals treated with the composition produced in example II and described in example III than in TNBS-treated animals (FIG. 9 and FIG. 10).

Example VII

HLA-B27 Rats

HLA-B27 transgenic rat, expressing HLA-B27 and human β2m, exhibits a phenotype similar to humans suffering B27 related rheumatic disorders such as reactive arthritis, ankylosing spondylitis, psoriasis and inflammatory bowel diseases. This rat model is useful for research and pharmacological studies of spontaneous systemic inflammation, arthritis, inflammatory bowel diseases and skin diseases including psoriasis and alopecia.

The primary goal of this example was to evaluate the in vivo efficacy of the composition produced in example II and described in example III in IBD present in HLA-B27 rat model. Basically, four group of ten (10) male HLA-B27 transgenic rats (7 to 20 weeks old) were formed following randomization which was based on the week of first symptoms of IBD (i.e. positive Hemoccult™). After one week of adaptation, the composition produced in example II and described in example III (7.82, 78.2 and 782 mg/kg) was orally administered daily via a gastric needle (total volume of 1.5 ml).

Figure 11:
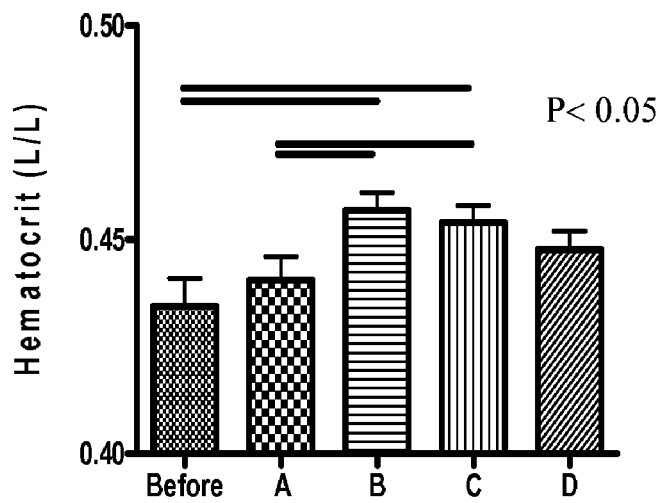
FIG. 11 shows hematocrit levels before and during oral treatment of HLA-B27 transgenic rats with different doses of the composition produced in example II and described in example III, where A is a placebo, B is the composition (7.82 mg/kg), C is the composition (78.2 mg/kg), and D is the composition (782 mg/kg), as described in detail in example VII.

Hematocrit. As shown in FIG. 11, hematocrit levels were higher in rats treated with 7.82 and 78.2 mg/kg of the composition produced in example II and described in example III compared to the value observed before the beginning of the treatment. Also, animals treated with 7.82 and 78.2 mg/kg of the composition produced in example II and described in example III had a higher level of hematocrit compared to placebo (PBS).

Figure 12:
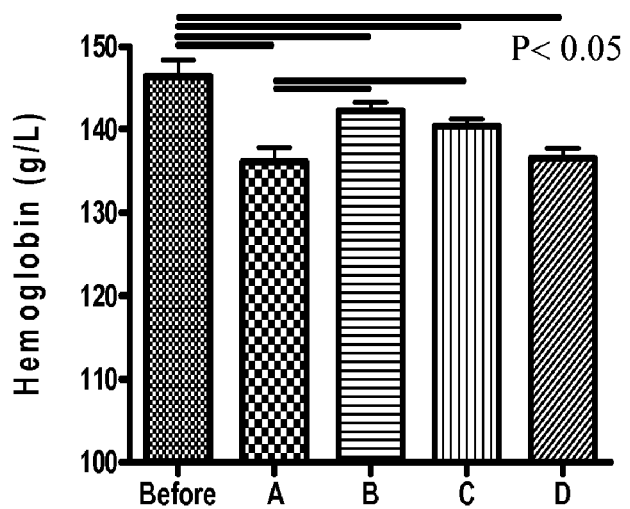
FIG. 12 shows hemoglobin levels before and during oral treatment of HLA-B27 transgenic rats with different doses of the composition produced in example II and described in example III, where A is a placebo, B is the composition (7.82 mg/kg), C is the composition (78.2 mg/kg), and D is the composition (782 mg/kg) as described in detail in example VII.

Hemoglobin. During the course of the disease, hemoglobin levels decreased significantly in all groups. However, the decrease was significantly lower in rats treated with 7.82 and 78.2 mg/kg of the composition produced in example II and described in example III compared to placebo or even to 782 mg/kg of the composition produced in example II and described in example III (FIG. 12).

Example VIII

Randomized Double-Blind, Placebo-Controlled Study

To validate the results from the open label study, a randomized, double-blind, placebo-controlled study was undertaken to confirm the efficacy and safety of XP-828L in the treatment of mild to moderate psoriasis (Poulin Y et al. (2006) *XP-828L in the treatment of mild to moderate psoriasis: randomized, double-blind, placebo-controlled study. J. Cutan. Med. Surg*).

Efficacy of XP-828L on Psoriasis

Intra-group analyses on efficacy parameters are shown in Table 9. The most significant improvement in patients treated with XP-828L was seen in PGA scores, which decreased significantly by 0.3±0.6 units (8.8±17.2%, $p<0.05$) from day 1 to day 56. This improvement was maintained at day 112 (0.3±0.5 units or 8.7±18.4%, $p<0.05$). Additional analyses showed that few significant interaction effects were detected in PGA scores in age and gender. However, patients over 50 years old reported a higher PGA score than younger patients at day 1 and day 112 ($p<0.05$) (data not shown).

BSA scores also improved in patients treated with XP-828L (Table 9). From day 1, BSA score improved by 0.5±1.7 units (5.9±17.3%, $p<0.05$) at day 56. The improvement was maintained at day 112. Significant differences in BSA score between genders (data not shown) were detected for day 1 ($p=0.006$), day 56 ($p=0.0016$) and day 112 ($p=0.017$), with men having a higher BSA score on average. Ten patients (24%) improved their BSA score by 25% and higher from their initial score and maintained this improvement under XP-828L. No significant differences were observed with age concerning the patients treated with XP-828L (data not shown).

PASI score improved from day 1 to day 56 ($p<0.05$). Eleven patients (26%) improved their PASI score by 25% and higher from initial score and maintained this improvement under XP-828L. On an individual basis, 5 patients out of 42 (11.9%) improved their PASI score by >40% in 56 days, while 8 patients out of 42 (19%) improved their PASI score by >40% during the entire study. PASI 50 was attained in 4 patients at day 56 and 6 patients at day 112. As for BSA, males reported a higher PASI score (data not shown) compared to female at each visit (Day 1, $p=0.009$; Day 56, $p=0.020$; Day 112, $p=0.022$). Itching sensation decreased significantly at day 112 for patients taking XP-828L ($p<0.05$) compared to day 1.

TABLE 9

Efficacy of the XP-828L at day 1, 56 and 112, as evaluated by different assessment tools.

|        | PASI          | PGA            | BSA           | Itch severity  |
|--------|---------------|----------------|---------------|----------------|
| Day 1  | 8.8 ± 3.9     | 3.0 ± 0.4      | 9.07 ± 4.32   | 1.6 ± 0.9      |
| Day 56 | 8.3 ± 4.3*    | 2.8 ± 0.6*     | 8.65 ± 4.78   | 1.3 ± 0.9      |
| Δ Abs. | −0.5 ± 1.8    | −0.3 ± 0.6*    | −0.5 ± 1.7    | −0.2 ± 0.9     |
| Δ %    | −5.8 ± 23.9   | −8.8 ± 17.2*   | −5.9 ± 17.3*  | −5.1 ± 63.8    |
| Day 112| 8.3 ± 4.4     | 2.8 ± 0.7      | 8.66 ± 5.53   | 1.3 ± 0.9*     |
| Δ Abs. | −0.5 ± 2.5    | −0.3 ± 0.5*    | −0.4 ± 3.5    | −0.3 ± 0.8*    |
| Δ %    | −4.9 ± 32.0   | −8.7 ± 18.4*   | −6.7 ± 33.2   | −12.0 ± 55.9   |

Note:
Data are mean ± SD of 42 human subjects.
*$p < 0.05$ compared to day 1. ΔAbs, absolute variation; Δ%, percent variation; PASI, psoriasis area and severity index; PGA, physician's global assessment; BSA, body surface area.

Figure 13:
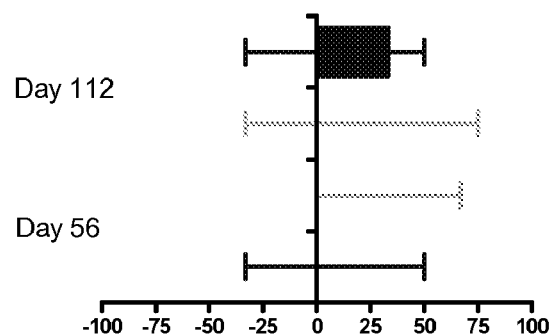
FIG. 13 shows the relative improvements or deterioration of primary and secondary endpoints from the double-blind, placebo-controlled study of Example VIII. The vast majority of the patients taking the composition improved all psoriasis assessment parameters from baseline at day 56 and day 112, indicating that patients could certainly benefit from further improvement with longer use of the present composition compared to a placebo; (●) XP-828L and (✻) placebo.
Figure 13:
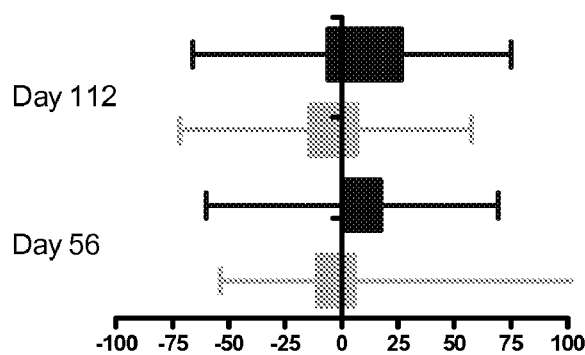
Figure 13:
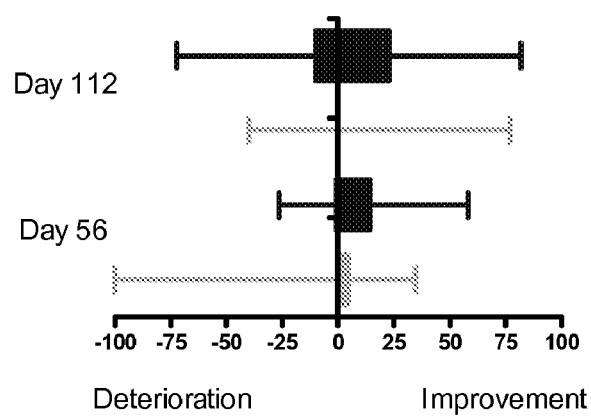
Figure 14:
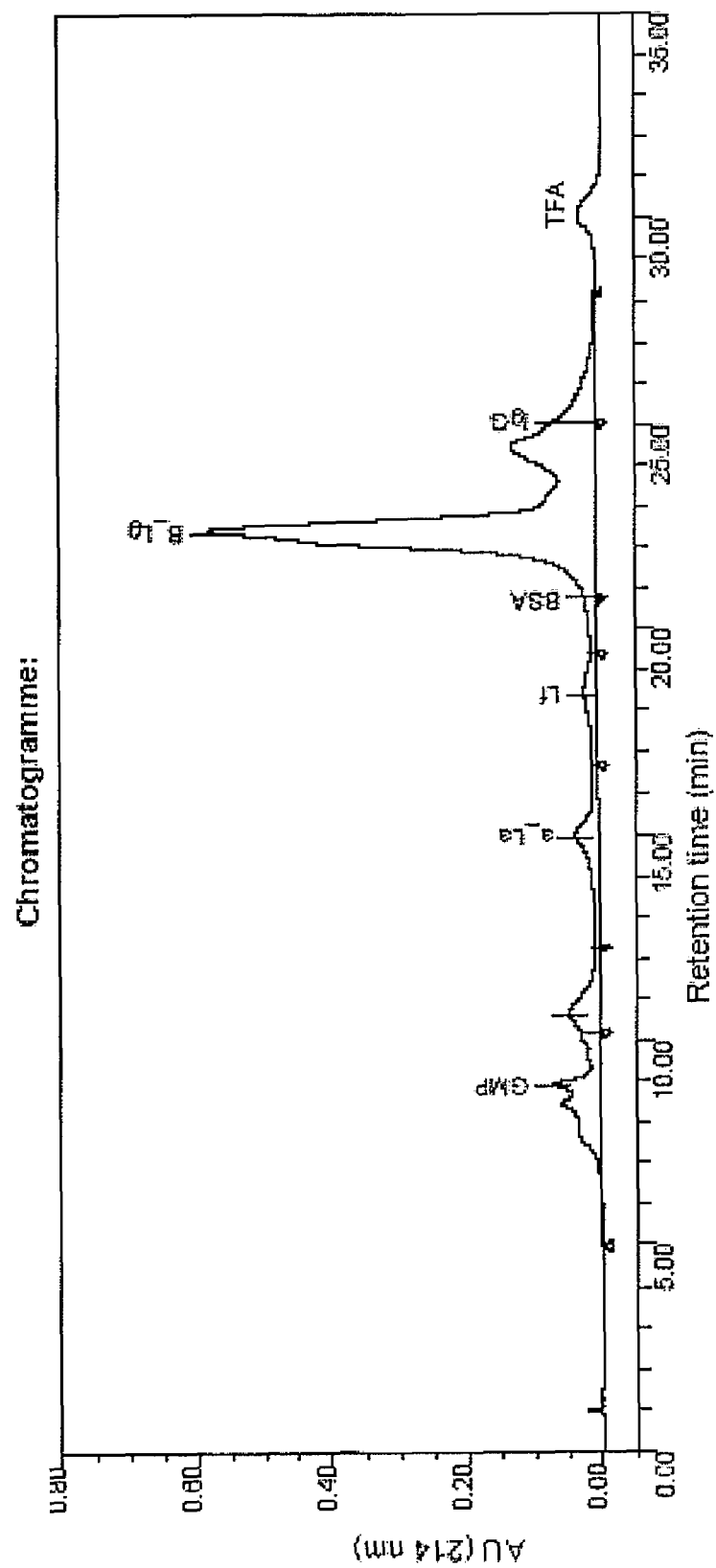
FIG. 14 represents a typical HPLC profile of the XP0828L composition.

Relative improvements of the study endpoints are illustrated in FIG. 13. As demonstrated, the vast majority of the patients improved all psoriasis assessment parameters from baseline at day 56 and day 112 indicating that patients could benefit from further improvement with longer use of XP-828L. PASI was improved as much as 25% in 8 patients at day 56 and in 11 patients at day 112. However, 2 patients show deterioration (>25%) at day 56 and 3 at day 112. Three patients improved their BSA score by 25% at day 56 and 6 at day 112, while no deterioration was seen at day 56 and only one at day 112. PGA also was improved in 9 and 12 patients at days 56 and 112, respectively, while only 2 patients showed deterioration at day 112, compared to baseline.

Prospective

Data available today suggest that XP-828L could modulate the inflammatory cascade seen in psoriasis through its systemic action on immune cells, mainly on T-lymphocytes. The proposed mechanism of action of XP-828L could also suggest a potential for the product to modulate in a beneficial way the immune system for the treatment or prevention of other immune-related diseases or other diseases related to an uncontrolled immune response like eczema and inflammatory bowel diseases.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A composition comprising Transforming Growth Factor (TGF)-β1 and TGF-β2, in admixture with proteins, wherein said TGF-β1 is at a concentration between 0.01 to 5 μg/g of the composition, said TGF-β2 is at a concentration between 5 to 50 μg/g of the composition, and said proteins are present in a concentration of at least 15% (w/w) of the composition and said proteins comprise at least 30% of β-lactoglobulin and less than 25% α-lactalbumin, wherein said TGF-β1, TGF-β2, proteins, β-lactoglobulin and α-lactalbumin are obtained from a single source of dairy product.

2. The composition of claim 1, wherein said proteins are present at a concentration of at least 50% (w/w), and comprises at least 60% of β-lactoglobulin.

3. The composition of claim 1, wherein said TGF-β1 is at a concentration between 0.1 to 5 μg/g of the composition.

4. The composition of claim 3, wherein said TGF-β1 is at a concentration between 0.2 to 1.2 μg/g of the composition.

5. The composition of claim 1, wherein said TGF-β2 is at a concentration between 8 to 20 μg per gram of the composition.

6. The composition of claim 5, wherein said TGF-β2 is at a concentration between 10 to 18 μg per gram of the composition.

7. The composition of claim 1, wherein said proteins obtained from dairy products are at a concentration of at least 80% (w/w) of the composition.

8. The composition of claim 1, comprising 0.1 to 15% (w/w) of minerals.

9. The composition of claim 1, further comprising Insulin-like Growth Factor-1 (IGF-1) obtained from the same source of dairy products as in claim 1.

10. The composition of claim 9, wherein said Insulin-like Growth Factor-1 (IGF-1) is at a concentration between 0.01 to 2 μg/g of the composition.

11. A method for the treatment of psoriasis comprising the step of: administering to a patient in need thereof a composition comprising: Transforming Growth Factor (TGF)-β1, TGF-β2, in admixture with proteins obtained from dairy products with a total protein concentration of at least 15% (w/w), wherein said TGF-β1 is at a concentration between 0.01 to 5 μg/g of composition, said TGF-β2 is at a concentration between 5 to 50 μg/g of composition, and said proteins obtained from dairy products contain at least 30% of β-lactoglobulin.

12. The method of treatment of claim 11, wherein said proteins obtained from dairy products are at a total protein concentration of at least 50% (w/w), and comprises at least 60% of β-lactoglobulin.

13. The method of treatment according to claim 11, wherein said TGF-β1 is at a concentration between 0.1 to 5 μg/g of composition.

14. The method of treatment according to claim 13, wherein said TGF-β1 is at a concentration between 0.2 to 1.2 μg/g of composition.

15. The method of treatment according to claim 11, wherein said TGF-β2 is at a concentration between 8 to 20 μg per gram of composition.

16. The method of treatment according to claim 14, wherein said TGF-β2 is at a concentration between 10 to 18 μg per gram of composition.

17. The method of treatment according to claim 11, wherein said dairy proteins are at a concentration of at least 80% (w/w) of the composition.

18. The method of treatment according to claim 11, comprising 0.1 to 15% (w/w) of minerals.

19. The method of treatment according to claim 11, wherein said TGF-β1 and said TGF-γ2 are derived from dairy products.

20. The method of treatment according to claim 11, further comprising Insulin-like Growth Factor-1 (IGF-1) derived from dairy products.

21. The method of treatment according to claim 19, wherein said Insulin-like Growth Factor-1 (IGF-1) is at a concentration between 0.01 to 2 μg/g of composition.

22. The composition of claim 1 or 9, wherein said dairy product is whey.

* * * * *